United States Patent [19]
Donehower et al.

[11] Patent Number: 5,569,824
[45] Date of Patent: Oct. 29, 1996

[54] TRANSGENIC MICE CONTAINING A DISRUPTED P53 GENE

[75] Inventors: Lawrence A. Donehower; Allan Bradley; Janet S. Butel, all of Houston; Betty Slagle, Bellaire, all of Tex.

[73] Assignee: Baylor College of Medicine, Houston, Tex.

[21] Appl. No.: 278,588

[22] Filed: Jul. 21, 1994

Related U.S. Application Data

[63] Continuation of Ser. No. 816,740, Jan. 3, 1992, abandoned, which is a continuation-in-part of Ser. No. 637,563, Jan. 4, 1991, abandoned.

[51] Int. Cl.$^6$ ............................ C12N 5/00; C12N 15/00; A61K 49/00
[52] U.S. Cl. .................................. 800/2; 424/9.1
[58] Field of Search ............................ 800/2; 435/172.3

[56] References Cited

U.S. PATENT DOCUMENTS

| | | | |
|---|---|---|---|
| 4,735,895 | 4/1988 | Kopelovich | 435/5 |
| 4,736,866 | 4/1988 | Leder et al. | 800/2 |
| 4,870,009 | 9/1989 | Evans et al. | 435/70 |

FOREIGN PATENT DOCUMENTS

| | | |
|---|---|---|
| WO82/04443 | 12/1982 | WIPO . |
| WO87/05325 | 9/1987 | WIPO . |
| WO87/07298 | 12/1987 | WIPO . |
| WO89/05864 | 6/1989 | WIPO . |
| WO90/05180 | 5/1990 | WIPO . |

OTHER PUBLICATIONS

Tybulewicz, V. L. J. et al., *Cell* 65:1153–1163 (1991).
Mucenski, M. L. et al., *Cell* 65:677–689 (1991).
McMahon, A. P. et al., *Cell* 62:1073–1085 (1990).
Soriano, P. et al., *Cell* 64:693–704 (1991).
Chen, P–L. et al., *Science* 250:1576–1580 (1990).
Jaenisch, R., *Science* 240:1468–1474 (1988).
Sager, R., *Science* 246:1406–1412 (1989).
Green, M. R., *Cell* 56:1–3 (1989).
Lane, D. P. et al., *Genes Develop.* 4:1–8 (1990).
Lavigueur, A. et al., *Molec. Cell. Biol.* 9:3982–3991 (1989).
Lee, W.–H. et al., *Science* 235:1394 (1987).
Takahashi, T. et al., *Science* 246:491–494 (1989).
Zakut–Houri, R. et al., *Nature* 306:594–597 (1983).
Malkin, D. et al., *Science* 250:1233–1238 (1990).
Cavenee, W. K. et al., *New Engl. J. Med.* 314:1201–1207 (1986).
Maitland, N. J. et al., *Anticanc. Res.* 9:1417–1426 (1989).
Marx, J., *Science* 250:1209 (1990).
Gossler, A. et al., *Proc. Natl. Acad. Sci. (U.S.A.)* 83:9065–9069 (1986).
Wagner, E. F. et al., *Cold Spring Harb. Symp. Quant. Biol* 50:691–700 (1985).
Brinster, R. L. et al., *Proc. Natl. Acad. Sci. (U.S.A.)* 86:7087–7091 (1989).
Capecchi, M. R., *Trends Genet.* 5:70–76 (1989).
Capecchi, M. R., *Science* 244:1288–1292 (1989).
Doetschman, T. et al., *Proc. Natl. Acad. Sci. (U.S.A.)* 85:8583–8587 (1988).
Evans, M. J. et al., *Nature* 292:154–156 (1981).
Evans, M. J. et al., *Cold Spring Harb. Symp. Quant. Biol.* 50:685–689 (1985).
Frohman, M. A. et al., *Cell* 56:145–147 (1989).
Thompson, S. et al., *Cell* 56:313–321 (1989).
Smithies, O. et al., *Nature* 317:230–234 (1985).
Schwartzberg, P. L. et al., *Science* 246:799–803 (1989).
Thomas, K. R. et al., *Cell* 51:503–512 (1987).
Mansour, S. L. et al., *Nature* 336:348–352 (1988).
Koller, B. H. et al., *Proc. Natl. Acad. Sci. (U.S.A.)* 86:8932–8935 (1989).
Koller, B. H. et al., *Proc. Natl. Acad. Sci. (U.S.A.)* 86:8927–8931 (1989).
Sedivy, J. M., *Bio–Technol.* 6:1192–1196 (1988).
Crawford, L. V., *Int. Rev. Exper. Pathol.* 25:1–50 (1983).
Bradley, A. et al., *Curr. Top. Devel. Biol.* 20:357–371 (1986).
Boggs, S. S. (*Int. J. Cell Clon.* 8:80–96 (1990).
Zijlstra, M. et al., *Nature* 342:435–438 (1989).
Zijlstra, M. et al., *Nature* 344:742–746 (1990).
Gough, N. M. et al., *Reprod. Fertil. Dev.* 1:281–288 (1989).
Gridley, T. et al., *Trends Genet.* 3:162 (1987).
Bradley, A. (In: *Teratocarcinomas and Embryonic Stem Cells: A Practical Approach*, (E. J. Robertson, Ed.), IRL Press, Oxford, 1987, pp. 113–151) (1989).

*Primary Examiner*—Jacqueline M. Stone
*Assistant Examiner*—Deborah Crouch
*Attorney, Agent, or Firm*—Burns, Doane, Swecker & Mathis

[57] ABSTRACT

A desired non-human animal or an animal cell or human cell which contains a predefined, specific and desired alteration in at least one of its two p53 chromosomal alleles, such that at least one of these alleles contains a mutation which alters the expression of the allele, and the other of the alleles expresses either a normal p53 gene product, or comprises an identical or different p53 mutation.

4 Claims, 5 Drawing Sheets

TRANSGENIC MICE CONTAINING A DISRUPTED P53 GENE

This is a Continuation of application Ser. No. 07/816,740, filed Jan. 3, 1992, now abandoned which is a CIP of Ser. No. 07/637,563, filed Jan. 4, 1991, abandoned.

FIELD OF THE INVENTION

The invention is directed toward tumor-susceptible non-human animals. The invention further pertains to the use of such animals in the development of anti-cancer agents and therapies.

BACKGROUND OF THE INVENTION

I. Chimeric and Transgenic Animals

Recent advances in recombinant DNA and genetic technologies have made it possible to introduce and express a desired gene sequence in a recipient animal. Through the use of such methods, animals have been engineered to contain gene sequences that are not normally or naturally present in an unaltered animal. The techniques have also been used to produce animals which exhibit altered expression of naturally present gene sequences.

The animals produced through the use of these methods are known as either "chimeric" or "transgenic" animals. In a "chimeric" animal, only some of the animal's cells contain and express the introduced gene sequence, whereas other cells have been unaltered. The capacity of a chimeric animal to transmit the introduced gene sequence to its progeny depends upon whether the introduced gene sequences are present in the germ cells of the animal. Thus, only certain chimeric animals can pass along the desired gene sequence to their progeny.

In contrast, all of the cells of a "transgenic" animal contain the introduced gene sequence. Consequently, every transgenic animal is capable of transmitting the introduced gene sequence to its progeny.

II. Production of Transgenic Animals: Microinjection Methods

The most widely used method through which transgenic animals have been produced involves injecting a DNA molecule into the male pronucleus of a fertilized egg (Brinster, R. L. et al., *Cell* 27:223 (1981); Costantini, F. et al., *Nature* 294:92 (1981); Harbers, K. et al., *Nature* 293:540 (1981); Wagner, E. F. et al., *Proc. Natl. Acad. Sci. (U.S.A.)* 78:5016 (1981); Gordon, J. W. et al., *Proc. Natl. Acad. Sci. (U.S.A.)* 73:1260 (1976); Stewart, T. A. et al., *Science* 217:1046–1048 (1982); Palmiter, R. D. et al., *Science* 222:809 (1983); Evans, R. M et al. (U.S. Pat. No. 4,870,009)).

The gene sequence being introduced need not be incorporated into any kind of self-replicating plasmid or virus (Jaenisch, R., *Science,* 240:1468–1474 (1988)). Indeed, the presence of vector DNA has been found, in many cases, to be undesirable (Hammer, R. E. et al., *Science* 235:53 (1987); Chada, K. et al., *Nature* 319:685 (1986); Kollias, G. et al., *Cell* 46:89 (1986); Shani, M., *Molec. Cell. Biol.* 6:2624 (1986); Chada, K. et al., *Nature* 314:377 (1985); Townes, T. et al., *EMBO J.* 4:1715 (1985)).

After being injected into the recipient fertilized egg, the DNA molecules are believed to recombine with one another to form extended head-to-tail concatemers. It has been proposed that such concatemers occur at sites of double-stranded DNA breaks at random sites in the egg's chromosomes, and that the concatemers are inserted and integrated into such sites (Brinster, R. L. et al., *Proc. Natl. Acad. Sci. (U.S.A.)* 82:4438 (1985)). Although it is, thus, possible for the injected DNA molecules to be incorporated at several sites within the chromosomes of the fertilized egg, in most instances, only a single site of insertion is observed (Jaenisch, R., *Science,* 240:1468–1474 (1988)).

Once the DNA molecule has been injected into the fertilized egg cell, the cell is implanted into the uterus of a recipient female, and allowed to develop into an animal. Since all of the animal's cells are derived from the implanted fertilized egg, all of the cells of the resulting animal (including the germ line cells) shall contain the introduced gene sequence. If, as occurs in about 30% of events, the first cellular division occurs before the introduced gene sequence has integrated into the cell's genome, the resulting animal will be a chimeric animal.

By breeding and inbreeding such animals, it has been possible to produce heterozygous and homozygous transgenic animals. Despite any unpredictability in the formation of such transgenic animals, the animals have generally been found to be stable, and to be capable of producing offspring which retain and express the introduced gene sequence.

Since microinjection causes the injected DNA to be incorporated into the genome of the fertilized egg through a process involving the disruption and alteration of the nucleotide sequence in the chromosome of the egg at the insertion site, it has been observed to result in the alteration, disruption, or loss of function of the endogenous egg gene in which the injected DNA is inserted. Moreover, substantial alterations (deletions, duplications, rearrangements, and translocations) of the endogenous egg sequences flanking the inserted DNA have been observed (Mahon, K. A. et al., *Proc. Natl. Acad. Sci. (U.S.A.)* 85:1165 (1988); Covarrubias, Y. et al., *Proc. Natl. Acad. Sci. (U.S.A.)* 83:6020 (1986); Mark, W. et al., *Cold Spr. Harb. Symp. Quant. Biol.* 50:453 (1985)). Indeed, lethal mutations or gross morphological abnormalities have been observed (Jaenisch, R., *Science* 240:1468–1474 (1988); First, N. L. et al., *Amer. Meat Sci. Assn. 39th Reciprocal Meat Conf.* 39:41 (1986))).

Significantly, it has been observed that even if the desired gene sequence of the microinjected DNA molecule is one that is naturally found in the recipient egg's genome, integration of the desired gene sequence rarely occurs at the site of the natural gene (Brinster, R. L. et al., *Proc. Natl. Acad. Sci. (U.S.A.)* 86:7087–7091 (1989)). Moreover, introduction of the desired gene sequence does not generally alter the sequence of the originally present egg gene.

Although the site in the fertilized egg's genome into which the injected DNA ultimately integrates cannot be predetermined, it is possible to control the expression of the desired gene sequence such that, in the animal, expression of the sequence will occur in an organ or tissue specific manner (reviewed by Westphal, H., *FASEB J.* 3:117 (1989); Jaenisch, R., *Science* 240:1468–1474 (1988); Meade, H. et al. (U.S. Pat. No. 4,873,316)).

The success rate for producing transgenic animals is greatest in mice. Approximately 25% of fertilized mouse eggs into which DNA has been injected, and which have been implanted in a female, will become transgenic mice. A lower rate has been thus far achieved with rabbits, sheep, cattle, and pigs (Jaenisch, R., *Science* 240:1468–1474 (1988); Hammer, R. E. et al., *J. Animal. Sci.* 63:269 (1986); Hammer, R. E. et al., *Nature* 315:680 (1985); Wagner, T. E.

et al., *Theriogenology* 21:29 (1984)). The lower rate may reflect greater familiarity with the mouse as a genetic system, or may reflect the difficulty of visualizing the male pronucleus of the fertilized eggs of many farm animals (Wagner, T. E. et al., *Theriogenology* 21:29 (1984)).

Thus, the production of transgenic animals by microinjection of DNA suffers from at least two major drawbacks. First, it can be accomplished only during the single-cell stage of an animal's life. Second, it requires the disruption of the natural sequence of the DNA, and thus is often mutagenic or teratogenic (Gridley, T. et al., *Trends Genet.* 3:162 (1987)).

III. Production of Chimeric and Transgenic Animals: Recombinant Viral and Retroviral Methods Chimeric and transgenic animals may also be produced using recombinant viral or retroviral techniques in which the gene sequence is introduced into an animal at a multi-cell stage. In such methods, the desired gene sequence is introduced into a virus or retrovirus. Cells which are infected with the virus acquire the introduced gene sequence. If the virus or retrovirus infects every cell of the animal, then the method results in the production of a transgenic animal. If, however, the virus infects only some of the animal's cells, then a chimeric animal is produced.

The general advantage of viral or retroviral methods of producing transgenic animals over those methods which involve the microinjection of non-replicating DNA, is that it is not necessary to perform the genetic manipulations at a single cell stage. Moreover, infection is a highly efficient means for introducing the DNA into a desired cell.

Recombinant retroviral methods for producing chimeric or transgenic animals have the advantage that retroviruses integrate into a host's genome in a precise manner, resulting generally in the presence of only a single integrated retrovirus (although multiple insertions may occur). Rearrangements of the host chromosome at the site of integration are, in general, limited to minor duplications (4–6 base pairs) of host DNA at the host virus junctions (Jaenisch, R., *Science* 240:1468–1474 (1988); see also, Varmus, H., In: *RNA Tumor Viruses* (Weiss, R. et al., Eds.), Cold Spring Harbor Press, Cold Spring Harbor, N.Y., pp. 369–512 (1982)). The method is, however, as mutagenic as microinjection methods.

Chimeric animals have, for example, been produced by incorporating a desired gene sequence into a virus (such as bovine papilloma virus or polyoma) which is capable of infecting the cells of a host animal. Upon infection, the virus can be maintained in an infected cell as an extrachromosomal episome (Elbrecht, A. et al., *Molec. Cell. Biol.* 7:1276 (1987); Lacey, M. et al., *Nature* 322:609 (1986); Leopold, P. et al., *Cell* 51:885 (1987)). Although this method decreases the mutagenic nature of chimeric/transgenic animal formation, it does so by decreasing germ line stability, and increasing oncogenicity.

Pluripotent embryonic stem cells (referred to as "ES" cells) are cells which may be obtained from embryos until the early post-implantation stage of embryogenesis. The cells may be propagated in culture, and are able to differentiate either in vitro or in vivo upon implantation into a mouse as a tumor. ES cells have a normal karyotype (Evans, M. J. et al., *Nature* 292:154–156 (1981); Martin, G. R. et al., *Proc. Natl. Acad. Sci. (U.S.A.)* 78:7634–7638 (1981)).

Upon injection into a blastocyst of a developing embryo, ES cells will proliferate and differentiate, thus resulting in the production of a chimeric animal. ES cells are capable of colonizing both the somatic and germ-line lineages of such a chimeric animal (Robertson, E. et al., *Cold Spring Harb. Conf. Cell Prolif.* 10:647–663 (1983); Bradley A. et al., *Nature* 309:255–256 (1984); Bradley, A. et al., *Curr. Top. Devel. Biol.* 20:357–371 (1986); Wagner, E. F. et al., *Cold Spring Harb. Symp. Quant. Biol.* 50:691–700 (1985); (all of which references are incorporated herein by reference).

In this method, ES cells are cultured in vitro, and infected with a viral or retroviral vector containing the gene sequence of interest. Chimeric animals generated with retroviral vectors have been found to have germ cells which either lack the introduced gene sequence, or contain the introduced sequence but lack the capacity to produce progeny cells capable of expressing the introduced sequence (Evans, M. J. et al., *Cold Spring Harb. Symp. Quant. Biol.* 50:685–689 (1985); Stewart, C. L. et al., *EMBO J.* 4:3701–3709 (1985); Robertson, L. et al., *Nature* (1986); which references are incorporated herein by reference).

Because ES cells may be propagated in vitro, it is possible to manipulate such cells using the techniques of somatic cell genetics. Thus, it is possible to select ES cells which carry mutations (such as in the hprt gene (encoding hypoxanthine phosphoribosyl transferase) (Hooper, M. et al., *Nature* 326:292–295 (1987); Kuehn, M. R. et al., *Nature* 326:295–298 (1987)). Such selected cells can then be used to produce chimeric or transgenic mice which fail to express an active HPRT enzyme, and thus provide animal models for diseases (such as the Lesch-Nyhan syndrome which is characterized by an HPRT deficiency) (Doetschman, T. et al., *Proc. Natl. Acad. Sci. (U.S.A.)* 85:8583–8587 (1988)).

As indicated above, it is possible to generate a transgenic animal from a chimeric animal (whose germ line cells contain the introduced gene sequence) by inbreeding.

The above-described methods permit one to screen for the desired genetic alteration prior to introducing the transfected ES cells into the blastocyst. One drawback of these methods, however, is the inability to control the site or nature of the integration of the vector.

IV. Production of Chimeric and Transgenic Animals: Plasmid Methods

The inherent drawbacks of the above-described methods for producing chimeric and transgenic animals have caused researchers to attempt to identify additional methods through which such animals could be produced.

Gossler, A. et al.,., for example, have described the use of a plasmid vector which had been modified to contain the gene for neomycin phosphotransferase (nptII gene) to transfect ES cells in culture. The presence of the nptII gene conferred resistance to the antibiotic G418 to ES cells that had been infected by the plasmid (Gossler, A. et al., *Proc. Natl. Acad. Sci. (U.S.A.)* 83:9065–9069 (1986), which reference is incorporated herein by reference). The chimeric animals which received the plasmid and which became resistant to G418, were found to have integrated the vector into their chromosomes.

Takahashi, Y. et al. have described the use of a plasmid to produce chimeric mice cells which expressed an avian crystallin gene (*Development* 102:258–269 (1988), incorporated herein by reference). The avian gene was incorporated into a plasmid which contained the nptII gene. Resulting chimeric animals were found to express the avian gene.

V. Introduction of Gene Sequences into Somatic Cells

DNA has been introduced into somatic cells to produce variant (chimeric) cell lines. hprt-deficient Chinese hamster ovary (CHO) cells have been transformed with the CHO hprt gene in order to produce a prototrophic cell line (Graf, L. H. et al., *Somat. Cell Genet.* 5:1031–1044 (1979)). Folger et al. examined the fate of a thymidine kinase gene (tk gene) which had been microinjected into the nuclei of cultured mammalian cells. Recipient cells were found to contain from 1 to 100 copies of the introduced gene sequence integrated as concatemers at one or a few sites in the cellular genome (Folger, K. R. et al., *Molec. Cell. Biol.* 2:1372–1387 (1982)). DNA-mediated transformation of an RNA polymerase II gene into Syrian hamster cells has also been reported (Ingles, C. et al., *Molec. Cell. Biol.* 2:666–673 (1982)).

Plasmids conferring host neomycin resistance and guanosine phosphotransferase activity have been transfected into Chinese hamster ovary cells to generate novel cell lines (Robson, C. N. et al., *Mutat. Res.* 163:201–208 (1986)).

VI. Oncogenes and Tumor Suppressor Genes

One mechanism through which cancer may arise is through a cell's exposure to a carcinogenic agent, either chemical or radiation. Such exposure may damage the DNA sequence of critical genes present in the genome of a cell of an animal. If this damage leads to either an impairment in the expression of the gene, or in the production of a mutant gene product, the cell may then proceed to proliferate, and ultimately result in the formation of a tumor.

One class of such critical genes has been referred to as "oncogenes." Oncogenes are genes which are naturally in an "inactivated" state, but which, through the effect of the DNA damage are converted to an "activated" state capable of inducing tumorigenesis (i.e. tumor formation). Oncogenes have been identified in 15–20% of human tumors. The products of oncogenes ("oncoproteins") can be divided into two broad classes according to their location in the cell.

Oncogene products which act in the cytoplasm of cells have readily identifiable biochemical or biological activities (Green, M. R., *Cell* 56:1–3 (1989)). Those that act in the nucleus of a cell have been more difficult to characterize. Some nuclear oncoproteins (such as E1A and myc) have transcriptional regulatory activity, and are believed to mediate their activities by the transcriptional activation of cellular genes (Kingston, R. E., *Cell* 41:3–5 (1985)). Other nuclear oncoproteins appear to have a complex array of activities (such as DNA binding activity, ability to initiate viral DNA synthesis, ATPase activity, helicase activity, and transcriptional regulatory activity) (Green, M. R., *Cell* 56:1–3 (1989)).

The creation of a mutant oncogene is only one of the requirements needed for tumor formation; tumorigenesis appears to also require the additional inactivation of a second class of critical genes: the "anti-oncogenes" or "tumor-suppressing genes." In their natural state these genes act to suppress cell proliferation. Damage to such genes leads to a loss of this suppression, and thereby results in tumorigenesis. Thus, the deregulation of cell growth may be mediated by either the activation of oncogenes or the inactivation of tumor-suppressing genes (Weinberg, R. A., *Scientific Amer.*, Sept. 1988, pp 44–51).

Oncogenes and tumor-suppressing genes have a basic distinguishing feature. The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny.

The classic example of a hereditary cancer is retinoblastomas in children. The incidence of retinoblastomas is determined by a tumor suppressor gene, the retinoblastoma (RB) gene (Weinberg, R. A., *Scientific Amer.*, Sept. 1988, pp 44–51); Hansen M. F. et al., *Trends Genet.* 4:125–128 (1988)). Individuals born with a lesion in one of the RB alleles are predisposed to early childhood development of retinoblastomas (Weinberg, R. A., *Scientific Amer.*, Sept. 1988, pp 44–51); Hansen M. F. et al., *Trends Genet.* 4:125–128 (1988)). Inactivation or mutation of (the second RB allele in one of the somatic cells of these susceptible individuals appears to be the molecular event that leads to tumor formation (Cavenee, W. K. et al., *Nature* 305:779–784 (1983); Friend, S. H. et al., *Proc. Nat'l. Acad. Sci. (U.S.A.)* 84:9059–9063 (1987)).

The RB tumor-suppressing gene has been localized onto human chromosome 13. The mutation may be readily transmitted through the germ line of afflicted individuals (Cavenee, W. K. et al., *New Engl. J. Med.* 314:1201–1207 (1986)). Individuals who have mutations in only one of the two naturally present alleles of this tumor-suppressing gene are predisposed to retinoblastoma. Inactivation of the second of the two alleles is, however, required for tumorigenesis (Knudson, A. G., *Proc. Nat'l. Acad. Sci. (U.S.A.)* 68:820–823 (1971)).

A second tumor-suppressing gene is the p53 gene (Green, M. R., *Cell* 56:1–3 (1989); Mowat et al., *Nature* 314:633–636 (1985)). The protein encoded by the p53 gene is a nuclear protein that forms a stable complex with both the SV40 large T antigen and the adenovirus E1B 55 kd protein. The p53 gene product may be inactivated by binding to these proteins.

Initially, the p53 gene was thought to be an oncogene rather than a tumor-suppressing gene since it is capable of immortalizing primary rodent cells and can cooperate with the ras oncogene to cause transformation. Subsequent research revealed that the p53 genes used in those early experiments was a mutant allele of the normal p53 gene (Green, M. R., *Cell* 56:1–3 (1989)). Thus, the p53 gene is a tumor-suppressing gene rather than an oncogene.

Mutations at any of a large number of positions in the p53 gene can result in the activation of the transforming potential of the p53 gene product (Eliyahu et al., *Nature* 312:646–649 (1984); Finlay et al., *Molec. Cell. Biol.* 8:531–539 (1988)). This has suggested that the activation of the p53 transforming activity is due to the inactivation of the normal p53 activity (Green, M. R., *Cell* 56:1–3 (1989)).

The p53 gene has been implicated as having a role in colorectal carcinoma (Baker, S. J. et al., *Science* 244:217–221 (1989)). Studies had shown that allelic deletions of the short arm of chromosome 17 occurred in over 75% of colorectal carcinomas. The region deleted was subsequently found to encompass the p53 gene locus (Baker, S. J. et al., *Science* 244:217–221 (1989)). The deletion of the region was found to mark a transition from a (benign) adenocarcinoma stage to a (malignant) carcinomatous stage (Vogelstein, B. et al., *New Engl. J. Med.* 319:525 (1988)).

Similar deletions in chromosome 17 have been identified in a wide variety of cancers including breast and lung cancers (Mackay, J. et al., *Lancet* ii:1384 (1988); James, C. D. et al., *Canc. Res.* 48:5546 (1988); Yakota, J. et al., *Proc. Nat'l. Acad. Sci. (U.S.A.)* 84:9252 (1987); Toguchida et al., *Canc. Res.* 48:3939 (1988)). In addition to p53 allele loss, Nigro et al. (*Nature* 342:705–708 (1989)) have demonstrated that the single remaining p53 allele in a variety of human tumors (brain, colon, breast, lung) undergo a point mutation which renders it tumorigenic. Fearon et al. (*Cell* 61:759–767 (1990)) have hypothesized that both point mutations and deletions in the p53 alleles may be required for a fully tumorigenic phenotype. These findings suggest that the p53 gene may have a role in many types of cancers.

VII. Conclusions

The application of the above-described technologies has the potential to produce animals which cannot be produced through classical genetics. For example, animals can be produced which suffer from human diseases (such as AIDS, diabetes, cancer, etc.), and may be valuable in elucidating therapies for such diseases. Chimeric and transgenic animals have substantial use as probes of natural gene expression.

Leder, P. et al, (U.S. Pat. No. 4,736,866) disclose the production of transgenic non-human mammals which contain cells having an exogenously added activated oncogene sequence. Although the animals are disclosed as being useful for assaying for carcinogenic materials, the precise location and structure of the added oncogene sequence in the animals is unknown, and cannot be experimentally controlled. Thus, the value of the animals as a model for oncogenesis is significantly impaired.

Despite the successes of the above-described techniques, the methods have not yet led to the development of a model transgenic animal which can be used to study the conditions responsible for the initiation of neoplasia, and which can be used as a means for developing suitable antineoplastic agents and therapies. Indeed, prior to the present invention, research on transgenic or chimeric animals containing mutations in oncogene and "critical" genes had suggested that it would not be possible to produce viable animals containing mutations in the chromosomal alleles of their tumor-suppressing genes. It was believed that such animals would be non-viable, or would not survive to maturity. See, Soriano, P. et al., *Cell* 64:693–702 (1991) [c-src]; McMahon, A. and Bradley, B., *Cell* 62:1073–1085 (1990) [Wnt-1]; Koller, B. et al., *Science* 248:1227–1230 (1990) [MHC-I]; Tybulewicz, V. L. J., *Cell* 65:1153–1164 (1991) [c-abl]; Mucenski, M. L., *Cell* 65:677–690 (1991) [c-myb].

If however, animals predisposed to cancer could be obtained, they would facilitate a better understanding of cancer; they could be used to assay for the presence of cancer-causing agents in food, waste products, etc.; they could also be used to identify agents capable of suppressing or preventing cancer. Such animals would, therefore, be extremely desirable. The present invention provides such animals, and the methods to produce and use them.

SUMMARY OF THE INVENTION

Figure 1:
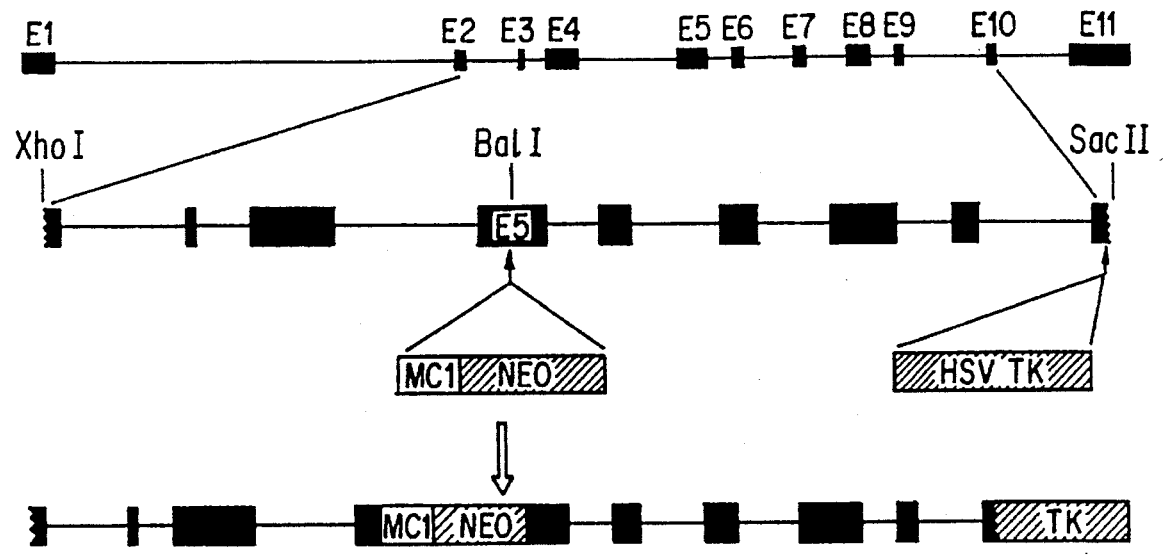
FIGS. 1(A–B) shows the modifications made to a 3.7-kb fragment spanning exons 2 to 10 of the 11 exon p53 gene in order to facilitate the construction of the transgenic animals of the present invention.
Figure 1A:
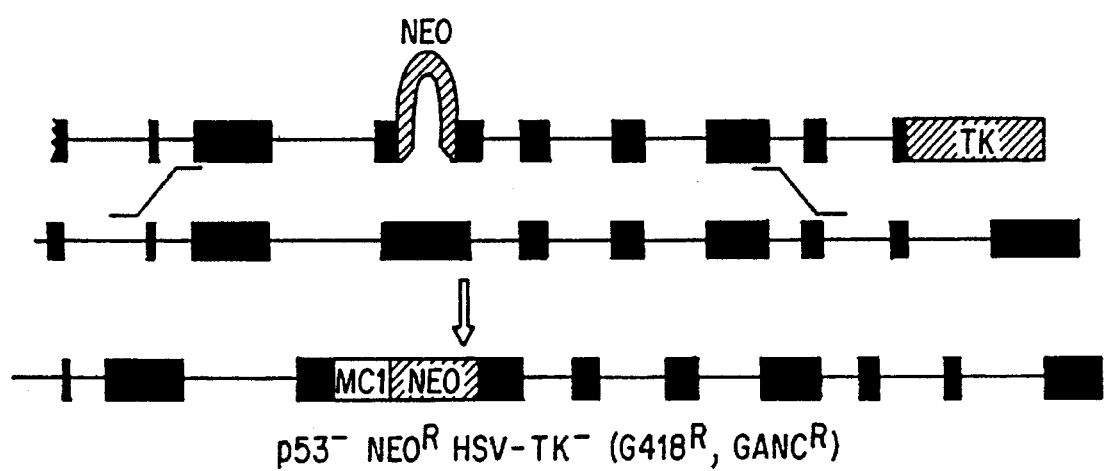
Figure 1B:
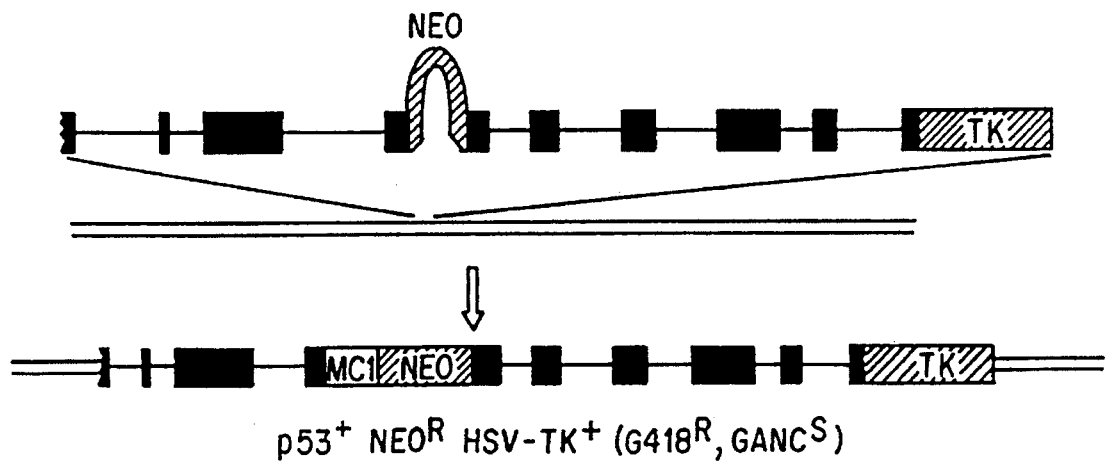

The present invention provides a desired non-human animal or an animal (including human) cell which contains a predefined, specific and desired alteration rendering the non-human animal or animal cell predisposed to cancer. Specifically, the invention pertains to a genetically altered non-human animal (most preferably, a mouse), or a cell (either non-human animal or human) in culture, that is defective in at least one of two alleles of a tumor-suppressor gene such as the p53 gene, the rb gene, etc., and most preferably, the p53 gene. The inactivation of at least one of these tumor suppressor alleles results in an animal with a higher susceptibility to tumor induction. A genetically altered mouse of this type is able to serve as a useful model for hereditary cancers and as a test animal for carcinogen studies. The invention additionally pertains to the use of such non-human animals or animal cells, and their progeny in research and medicine.

In detail, the invention provides a transgenic or chimeric animal cell whose genome comprises two chromosomal alleles of a tumor-suppressing gene (especially, the p53 gene), wherein at least one of the two alleles contains a mutation, or the progeny of this cell.

The invention includes the embodiment of the above animal cell, wherein one of the alleles expresses a normal tumor-suppressing gene product.

The invention includes the embodiments wherein the above animal cells are human cells, or the cells of a non-human animal. The invention includes the embodiment wherein the cell is an embryonic stem cell, and in particular, wherein the tumor-suppressing gene is a p53 gene, and the embryonic stem cell is ATCC CRL 10631.

The invention also includes a non-human transgenic or chimeric animal having an animal cell whose genome comprises two chromosomal alleles of a tumor-suppressing gene, wherein at least one of the two alleles contains a mutation, or the progeny of the animal, or an ancestor of the animal, at an embryonic stage (preferably the one-cell, or fertilized oocyte stage, and generally, not later than about the 8-cell stage).

The invention also includes the embodiment wherein the tumor suppressing gene of the non-human animal is a p53 gene.

The invention is also directed to the embodiments wherein the animal cell of the non-human animal is a human cell, or a cell of a non-human animal (of either the same species as the non-human animal or a different species).

The invention is also directed to the embodiments wherein the animal cell of the non-human animal is a germ-line cell, or a somatic cell.

The invention is also directed to the embodiment wherein the animal cell of the non-human animal is an embryonic stem cell (especially the embryonic stem cell, ATCC CRL 10631).

The invention additionally provides a method for identifying the presence of an agent suspected of being capable of affecting a characteristic of an animal cell that is attributable to the presence or expression of a tumor-suppressing gene, the method comprising:

A) administering an amount of the agent to an animal cell in cell culture, the cell having a genome that comprises two chromosomal alleles of the tumor-suppressing gene, wherein at least one of the two alleles contains a mutation;

B) maintaining the cell culture for a desired period of time after the administration;

C) determining whether the administration of the agent has affected a characteristic of the animal cell that is attributable to the presence or expression of the alleles of the tumor-suppressing gene.

In particular, the invention includes the embodiment of the above method wherein the tumor-suppressing gene is a p53 gene.

The invention also includes the embodiments of this method wherein the agent is suspected of being able to increase a tumorigenic potential of the animal cell, wherein the agent is suspected of being able to decrease a tumorigenic potential of the animal cell, wherein the animal cell is a human cell, and wherein the animal cell is a non-human animal cell (such as an embryonic stem cell, and in particular, the embryonic stem cell, ATCC CRL 10631).

The invention also provides a method for identifying the presence of an agent suspected of being capable of affecting a characteristic of an animal cell that is attributable to the presence or expression of a tumor-suppressing gene, the method comprising:

A) administering an amount of the agent to an animal, the animal having a cell whose genome comprises two chromosomal alleles of the tumor-suppressing gene, wherein at least one of the two alleles contains a mutation;

B) maintaining the animal for a desired period of time after the administration;

C) determining whether the administration of the agent has affected a characteristic of the cell that is attributable to the presence or expression of the alleles of the tumor-suppressing gene.

In particular, the invention includes the embodiments of the above method wherein the tumor-suppressing gene is a p53 gene.

The invention also includes the embodiments of this method wherein the agent is suspected of being able to increase a tumorigenic potential of the animal cell, wherein the agent is suspected of being able to decrease a tumorigenic potential of the animal cell, wherein the animal cell is a human cell, and wherein the animal cell is a non-human animal cell (such as an embryonic stem cell, and in particular, the embryonic stem cell, ATCC CRL 10631).

The invention also includes the embodiments of this method wherein the animal and the animal cell are of the same species, of different species.

The invention further provides a method of gene therapy comprising altering the genome of a cell of either a human or a non-human animal, wherein the cell has a genome that comprises two chromosomal alleles of a tumor-suppressing gene, and wherein at least one of the two alleles contains a mutation, to thereby form a cell wherein at least one of the alleles expresses a normal tumor-suppressing gene product.

In particular, the invention includes the embodiments of the above method of gene therapy wherein the tumor-suppressing gene is a p53 gene.

DESCRIPTION OF THE PREFERRED EMBODIMENTS

As is well known, the cells of humans and animals (especially, rodents (i.e. mouse, rat, hamster, etc.), rabbits, sheep, goats, fish, pigs, cattle and non-human primates) are "diploid" cells, and thus naturally contain two copies ("alleles") of each and every gene of their genome. A cell's "genome" consists of all of its heritable DNA (either chromosomal or non-chromosomal (i.e. episomal, viral, etc.). One of the two alleles of a gene is provided by the animal's or cell's maternal parent; the other set is provided by its paternal parent. The diploid nature of human and animal cells is described by DeRobertis, E. D. P., et al. (*Cell Biology*, 6th Ed., W. B. Saunders Company, Philadelphia, (1975)), and in other similar treatises of cell biology.

Cancer in humans develops through a multi-step process, indicating that multiple changes must occur to convert a normal cell into one with a malignant phenotype. One class of involved genes includes cellular oncogenes. When activated by mutation or when expressed inappropriately, dominant-acting oncogenes override normal cellular control mechanisms and promote unbridled cell proliferation. A newly recognized class of cellular genes that appears to be equally important in cancer development includes the tumor suppressor genes, sometimes called "anti-oncogenes." These genes act to dampen cell growth; inactivation of their normal function appears to be a common denominator in the evolution of tumor cells. Both alleles of a tumor suppressor gene must be inactivated to result in loss of function in the cell. Inactivation of one allele (i.e., the gene copy on one of the two chromosomes) increases the probability that an event will damage the surviving allele, in effect making the host more susceptible to tumor induction.

The present invention relates to the production of non-human transgenic and chimeric animals and cells which contain at least one mutated chromosomal allele of a tumor suppressor gene (and, in a preferred embodiment, one normal allele of that gene). Where the cells and non-human animals of the present invention contain mutations in both of their chromosomal alleles, such mutations may be the same, or they may be different from one another.

As is well known, an allele may be capable of being expressed by the natural processes operating in a cell. The expression of an allele results in the production of a gene product. The term "allele" as used herein is intended to denote any nucleotide sequence that affects the expression of a particular gene. It thus is intended to refer to any enhancer, promoter, processing, intervening, coding or termination sequence or region of the gene, or any sequence that stabilizes the gene product, or its mRNA, etc.

An allele of a gene is said to be mutated if (1) it is not expressed in a cell or animal, (2) the expression of the allele is altered with respect to the expression of the normal allele of the gene, or (3) the allele expresses a gene product, but that gene product has altered structure, activity, or characteristics relative to the gene product of a normal allele of that gene.

Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. A "normal tumor-suppressing gene product" is the gene product that is expressed by a "normal" tumor-suppressing gene.

A mutation may be "cryptic." A cryptic mutation does not affect either the expression of the mutated gene, or the activity or function of the expressed gene product. Cryptic mutations may be detected through nucleotide sequence analysis. Examples of cryptic mutations include mutations that do not result in a change in the amino acid sequence of the expressed gene product, as well as mutations that result in the substitution of an equivalent amino acid at a particular position in the expressed gene product. Most preferably, the mutation will be "non-cryptic" and will therefore introduce a change in the nucleotide sequence of the allele that detectably alters either the expression or the activity or function of the allele. A "mutation that detectably alters the expression of an allele," as used herein denotes any change in nucleotide sequence affecting the extent to which the allele is transcribed, processed or translated. Such alterations may be, for example, in an enhancer, promoter, coding or termination region of the allele, mutations which stabilize the gene product, or its mRNA, etc. A "mutation that detectably alters the activity of an allele," as used herein denotes any change in nucleotide sequence that alters the capacity of the expressed gene product to mediate a function of the gene product. Such mutations include changes that diminish or inactivate one or more functions of the expressed product. Significantly, such mutations also include changes that result in an increase the capacity of the gene product to mediate any function (for example, a catalytic or binding activity) of that gene product. A "mutation that detectably alters the function of an allele," as used herein denotes any change in nucleotide sequence that alters the capacity of a binding molecule (such as a binding protein) to specifically bind to the allele.

Any of a wide variety of methods (treatment with mutagenic compounds, spontaneous isolation, insertional inactivation, site-specific insertions, deletions or substitutions, homologous recombination, etc.) may be used to produce mutations in accordance with the present invention. As indicated above, a large number of such mutations are known, and mutations can be readily identified by sequencing, tumorigenicity, resilience to tumorigenicity, binding activity, etc. (see, for example, Eliyahu et al., *Nature* 312:646–649 (1984); Finlay et al., *Molec. Cell. Biol.* 8:531–539 (1988); Nigro, J. M. et al., *Nature* 342:705–708 (1989), all herein incorporated by reference).

An allele is said to be "chromosomal" if it either is, or replaces, one of the two alleles of a gene which a cell inherits from its ancestors, or which an animal inherits from its parents. An allele is not "chromosomal," as that term is used herein, if the allele increases the copy number of the total number of alleles of a particular gene which are present in a cell.

The cells that can be produced in accordance with the present invention include both "germ-line" and "somatic" cells. A germ-line cell is a sperm cell or egg cell, or a precursor or progenitor of either; such cells have the potential of transmitting their genome (including the altered tumor-suppressor allele) in the formation of progeny animals. A somatic cell is a cell that is not a germ-line cell. Such cells may be "substantially free of naturally occurring contaminants," or may be present in an animal of the same or of different species. A cell is "substantially free of naturally occurring contaminants" when it, or a precursor or ancestor cell, has been purified from tissue (normal, tumor, etc.) in which the cell is, or would be, naturally associated. Two species are said to be the same if they are capable of breeding with one another to produce fertile offspring. Two species are said to be different if they are either incapable of breeding to produce viable offspring, or are substantially incapable of producing fertile offspring.

The present invention encompasses the formation of such cells and non-human animals for any tumor suppressor gene. Examples of such genes include the rb gene (Weinberg, R. A., *Scientific Amer.*, Sept. 1988, pp 44–51); Hansen M. F. et al., *Trends Genet.* 4:125–128 (1988)), the gene responsible for Wilms tumor (Maitland, N. J. et al., *Anticanc. Res.* 9:1417–1426 (1989); Shaw, A. P. W. et al., *Oncogene* 3:143–150 (1988); Kovacs, G. et al., *Proc. Natl. Acad. Sci. (U.S.A.)* 85:1571–1575 (1988); Kumar, S. et al., *Int. J. Canc.* 40:499–504 (1987); Allen, D. M. et al., *Clin. Res.* 35:416A (1987)) and the p53 gene (Lane, D. P. et al., *Genes & Develop.* 4:1–8 (1990)). Other tumor suppressor genes may, however, be used in accordance with the present invention (Hiti, A. L., *Molec. Cell. Biol.* 9:4722–4730 (1989); Hastie, N., *Anticanc. Res.* 8:1074 (1988); Boada, M. B., *Oncologia* 10:9–30 (1987); Gallie, B. L., *J. Cell. Biochem.* 32:215–222 (1986); Alt, F. W. et al., *Cold Spr. Harb. Symp. Quant. Biol.* 51:931–942 (1986); Knudson, A. G., *Symp. Molec. Cell. Biol. Biochem. Molec. Epidemiol. Canc.* 40:6–13 (1985); Malcolm, S. *Molec. Med.* 1:79–94 (1984); Tricoli, J. et al. *Amer. J. Hum. Genet.* 36:121S (1984); all herein incorporated by reference).

The rb and p53 genes are the preferred tumor suppressor genes of the present invention. The cDNA and genomic forms of the rb gene have been cloned (Friend, S. et al., *Nature* 323:643 (1986); Lee, W. et al., *Science* 235:1394 (1987); Fung, Y. et al., *Science* 236:1657 (1987); Hong, F. et al., *Proc. Nat'l. Acad. Sci. (U.S.A.)* 86:5502 (1989), all herein incorporated by reference). Potential methods and animal (including transgenic) models for the study of retinoblastoma are discussed in Lee, W. et al., WO 90/05180, herein incorporated by reference. The invention is illustrated below with reference to the p53 tumor suppressor gene. The ability to manipulate this gene and to produce non-human transgenic animals which carry such mutated alleles is illustrated with respect to a particular mutated allele. It is to be understood, however, that the invention and the methods disclosed herein, can be used to produce any possible mutation in the p53 gene. In particular, the invention includes the production of animal cells and non-human transgenic or chimeric animals which carry the particular mutations of the p53 gene that are responsible for the Li-Fraumeni Syndrome discussed below.

I. The p53 Gene

The present invention concerns a non-human animal or an animal (including human) cell in which one of the two naturally present copies of the p53 gene of such non-human animal or animal cell has been rendered non-functional through a mutation (such as a deletion, insertion, or substitution in the naturally occurring p53 gene sequence).

The normal p53 gene product is a tumor-suppressing protein (Sager, R., *Science* 246:1406–1412 (1989); Finlay, C., *Cell* 57:1083 (1989), both of which references are herein incorporated by reference). The nature and characteristics of the p53 gene is reviewed by Lane, D. et al. (*Genes Devel.* 4:1–8 (1990), herein incorporated by reference). The p53 gene plays a protective role against the transforming effects of Friend erythroleukemia virus (Munroe, D. et al. *Oncogene* 2:621 (1988)). It is also believed to play a role in chromosome stability, differentiation and senescence, and cell proliferation (Sager, R., *Science* 246:1406–1412 (1989)).

As indicated above, allelic deletions of the p53 locus have been identified in colorectal carcinomas. Mutations in the p53 gene have also been identified in tumors of the brain, breast, and lung (including bronchioalveolar carcinoma, extrapulmonary small cell carcinoma, adenocarcinoma, small cell carcinoma, adenosquamous carcinoma, pulmonary carcinoid tumors, and in a neurofibrosarcoma (Nigro, J. M. et al., *Nature* 342:705–708 (1989); Takahashi, T. et al., *Science* 246:491–494 (1989)). Most tumors with such allelic deletions contain p53 point mutations resulting in amino acid substitutions. Such mutations are not confined to tumors with such allelic deletions, but also occur in some tumors that have retained both parental alleles. Mutations in the p53 gene which give rise to tumors are associated in four "hot-spots" which coincide with the most highly conserved sequences of the p53 gene (Nigro, J. M. et al., *Nature* 342:705–708 (1989), herein incorporated by reference).

In summary, there is now convincing evidence that the human p53 gene is a tumor suppressor gene (Weinberg, R. A., *Scientific Amer.*, Sept. 1988, pp 44–51). Like the RB protein, discussed above, p53 is a nuclear protein that forms a complex with SV40 large T antigen (DeCaprio, J. A. et al., *Cell* 54:275–283 (1988); Crawford, L. V., *Int. Rev. Exper. Pathol.* 25:1–50 (1983)). The binding of these two proteins by viral tumor antigens presumably inactivates them and contributes to transformation. p53 gene deletions have been noted in several mouse erythroleukemic cell lines, reminiscent of the RB gene deletions in retinoblastomas (Mowat et al., *Nature* 314:633–636 (1985); Chow et al., *J. Virol.* 61:2777–2781 (1987); Hicks, G. G. et al., *J. Virol.* 62:4752–4755 (1988)). Cell lines and tumors derived from human osteogenic sarcomas often contain gross rearrangements of the p53 gene, including deletions (Masuda, H., *Proc. Nat'l. Acad. Sci. (U.S.A.)* 84:7716–7719 (1987)). Allelic deletions in chromosome 17p (which contains the p53 gene) occur in over 75% of colorectal carcinomas (Baker, S. J. et al., *Science* 244:217–221 (1989)). In two tumors, the remaining non-deleted p53 allele was shown to contain mutants in highly conserved regions previously found to be mutated in murine p53 genes (Baker, S. J. et al., *Science* 244:217–221 (1989)). Loss of heterozygosity in chromosome 17p has been noted in a high percentage of individuals with small cell lung carcinoma (Yokoto, J. et al., *Proc. Nat'l. Acad. Sci. (U.S.A.)* 84:9252–9526 (1987); Harbour, J. W. et al., *Science* 241:353–356 (1988)). In the HL-60 human leukemic cell line, major deletions in the p53 gene and absence of the p53 protein have been noted (Wolf, D. et al., *Proc. Nat'l. Acad. Sci. (U.S.A.)* 82:790–794 (1985)). These results indicate that the absence of a functional p53 allele is highly correlated with some forms of cancer in humans and mice, strongly suggesting a tumor-suppressor role for p53. Finally, Finlay et al. (*Cell* 57:1083–1093 (1989)) have recently demonstrated that the wild-type mouse p53 gene suppresses transformation in vitro after cotransfection of rat embryo cells with E1a and activated ras, indicating that the presence of the normal p53 gene acts negatively to block transformation.

The cDNA and genomic forms of the p53 gene have been cloned (Pennica, D. et al., *Virol.* 134:477–482 (1984); Jenkins, J. et al., *Nature* 312:651–654 (1984); Oren, M. et al., *EMBO J.* 2:1633–1639 (1983); Zahut-Houri, R. et al., *Nature* 306:594–597 (1983), all of which references are herein incorporated by reference).

Recent evidence has suggested that a mutation in the p53 gene may be responsible for the Li-Fraumeni Syndrome, a rare human genetic disorder (Malkin, D. et al., *Science* 250:1233–1238 (1990); Marx, J., *Science* 250:1209 (1990), both references herein incorporated by reference). Individuals afflicted with this disease are highly susceptible to several malignant tumors—breast carcinomas, soft tissue sarcomas, brain tumors, osteosarcomas, leukemia, and adrenocortical carcinoma. The disease is also associated with a higher incidence of melanoma, gonadal germ cell tumors, and carcinomas of the lung, pancreas and prostate (Li, F. P. et al., *Ann. Intern. Med.* 71:747 (1969); Birch, J. M. et al., *J. Clin. Oncol.* 8:583 (1990); Birch, J. M. et al., *Brit. J. Canc.* 49:325 (1984); Li, F. P. et al., *Canc. Res.* 48:5358 (1988); Williams, W. R. et al., *Familial Canc.*, 1st Int. Res. Conf. p. 151 (Karger, Basel, 1985); Strong, L. C. et al., *J. Natl. Canc. Inst.* 79:1213 (1987)).

The Li-Fraumeni Syndrome is associated with a particular set of mutations in exon 7 of the p53 gene (Malkin, D. et al., *Science* 250:1233–1238 (1990), herein incorporated by reference). Knowledge of the sequence and location of the mutation which causes the Li-Fraumeni syndrome permits one to use the methods of the present invention to produce a non-human transgenic animal which contains any of these mutations. As indicated above, such an animal, and its uses in diagnostics and gene therapy, is an embodiment of the present invention.

II. The Interaction of Mutant and Normal p53 Gene Products

A cascade of mutational events is believed to be required for tumorigenesis. It is believed that this cascade involves both the activation of one or more oncogene(s) and the inactivation of one or more tumor-suppressing gene(s) (Sager, R., *Science* 246:1406–1412 (1989); Fearson, E. R. et al., *Cell* 61:759–767 (1990), both herein incorporated by reference). Indeed, mutations in at least 4–5 genes are believed to be required for the formation of a malignant tumor.

Studies of the clonal nature of tumor formation have suggested that tumors have a monoclonal composition, and hence arise by the clonal propagation of a single progenitor cell (Fearson, E. R. et al., *Science* 247:193–197 (1987)). The loss (either by mutation or deletion) of functional p53 gene function has been found to be a characteristic of colorectal tumors (Fearson, E. R. et al., *Cell* 61:759–767 (1990)).

The simplest model to explain the mechanism of action of a tumor-suppressing gene is that malignancy requires two separate genetic events (i.e. loss by deletion or mutation of both functional p53 alleles in a cell). Inactivation of only one of the two natural p53 alleles causes a phenotypically silent, recessive mutation which does not result in malignancy in the absence of the second mutational event.

It has been observed that, by introducing DNA containing a mutated p53 gene into rodent cells, such cells can be transformed. This transformation is due to a cooperative action of the mutant p53 gene product with the gene product of the ras oncogene. Since such cells also express the normal p53 gene, it has been proposed that the inactivation of only one p53 allele is not phenotypically silent (Fearson, E. R. et al., *Cell* 61:759–767 (1990)). The ability of the cells to undergo transformation in the presence of both the normal and the mutant p53 gene products suggests that the two gene products may interact to exert their effects. One explanation of the mixed recessive-dominant characteristic of the p53 mutant/normal allele interaction is that oligomerization is needed for activity, and that the oligomer formed in cells having both a mutant and a normal p53 allele contains a mixture of the gene products of these alleles (Eliyahu et al., *Oncogene* 3:313–321 (1988); Kraiss, et al., *J. Virol.* 62:4737–4744 (1988)). Due to the presence of the mutant p53 gene product in such mixed oligomers, the oligomers would be expected to have a diminished ability to suppress tumor formation (Fearson, E. R. et al., *Cell* 61:759–767 (1990), herein incorporated by reference). Consistent with this explanation has been the finding that mutant p53 gene products form heterodimers with the wild-type p53 gene product (Finlay, C. A., *Cell* 57:1083 (1989)).

Transgenic animals may be used to investigate the biological implications of tumor-suppressing genes (Capecchi, M. R., *Science* 244:1288–1292 (1989)). Lavigueur, A. et al. constructed a transgenic mouse which had a single added mutant p53 gene in addition to the endogenous two wild-type p53 alleles. The mouse, and its progeny overexpressed the added p53 gene. The mice were found to have a high incidence of lung, bone, and lymphoid tumors (Lavigueur, A. et al., *Molec. Cell. Biol.* 9:3982–3991 (1989). The high levels of mutant p53 in these mice led to tumor formation in 22 of 112 mice examined. Due to the overexpression of the mutant p53 gene product, and to the ability of this mutant protein to impair the biological activity of the normal p53 gene product, the transgenic mice of Lavigueur et al. exhibit the phenotype of an animal in which all normal, endogenous p53 gene product activity has been functionally inactivated (Lavigueur, A. et al., *Molec. Cell. Biol.* 9:3982–3991 (1989); Sager, R., *Science* 246:1406–1412 (1989)).

Thus, the mice described by Lavigueur, A. et al. (*Molec. Cell. Biol.* 9:3982–3991 (1989)) contained an added oncogenic p53 allele in addition to its two normal p53 genes. Importantly, the effect of gene dosage in such animals is unknown. Moreover, it is not known whether the added p53 gene in such animals contains all of the normal upstream and downstream regulatory elements. Even if all of such elements were present, the context of the integration of the construct may render the regulation of the gene abnormal. For these reasons, the utility of the mice in assessing the role of the p53 gene on oncogenesis is unclear.

It would be desirable to produce a transgenic animal whose genome possesses one normal and functional p53 allele and one non-functional (mutant) p53 allele. Such animals could be used to study the consequences resulting from the loss of one p53 allele, and thus would more clearly aid in elucidating the processes of oncogenesis and tumorigenesis. Such animals would also be useful in screening potential carcinogens, in developing novel antineoplastic therapeutics, and in gene therapy. The present invention provides such an animal.

III. Homologous Recombination

The present invention uses the process of homologous recombination to introduce a specific mutation into the naturally present p53 sequence of an animal cell, most preferably an embryonic stem (ES) cell. The mutated ES cells of non-human animals can then be either cultured in suitable cell culture medium, or introduced into the uterus of a suitable recipient and permitted to develop into a non-human animal.

Alternatively, the methods of the present invention may be used to alter the somatic cells of a non-human animal to produce a chimeric non-human animal.

An understanding of the process of homologous recombination (Watson, J. D., In: *Molecular Biology of the Gene*, 3rd Ed., W. A. Benjamin, Inc., Menlo Park, Calif. (1977), which reference is incorporated herein by reference) is thus desirable in order to fully appreciate the present invention.

In brief, homologous recombination is a well-studied natural cellular process which results in the scission of two nucleic acid molecules having identical or substantially similar sequences (i.e. "homologous"), and the ligation of the two molecules such that one region of each initially present molecule is now ligated to a region of the other initially present molecule (Sedivy, J. M., *Bio-Technol.* 6:1192–1196 (1988), which reference is incorporated herein by reference).

Homologous recombination is, thus, a sequence specific process by which cells can transfer a "region" of DNA from one DNA molecule to another. As used herein, a "region" of DNA is intended to generally refer to any nucleic acid molecule. The region may be of any length from a single base to a substantial fragment of a chromosome.

For homologous recombination to occur between two DNA molecules, the molecules must possess a "region of homology" with respect to one another. Such a region of homology must be at least two base pairs long. Two DNA molecules possess such a "region of homology" when one contains a region whose sequence is so similar to a region in the second molecule that homologous recombination can occur.

Recombination is catalyzed by enzymes which are naturally present in both prokaryotic and eukaryotic cells. The transfer of a region of DNA may be envisioned as occurring through a multi-step process.

If either of the two participant molecules is a circular molecule, then the recombination event results in the integration of the circular molecule into the other participant.

Importantly, if a particular region is flanked by regions of homology (which may be the same, but are preferably different), then two recombinational events may occur, and result in the exchange of a region of DNA between two DNA molecules. Recombination may be "reciprocal," and thus results in an exchange of DNA regions between two recombining DNA molecules. Alternatively, it may be "non-reciprocal," (also referred to as "gene conversion") and result in both recombining nucleic acid molecules having the same nucleotide sequence. There are no constraints regarding the size or sequence of the region which is exchanged in a two-event recombinational exchange.

The frequency of recombination between two DNA molecules may be enhanced by treating the introduced DNA with agents which stimulate recombination. Examples of such agents include trimethylpsoralen, UV light, etc.

IV. Production of Chimeric and Transgenic Animals: Gene Targeting Methods

One approach to producing animals having defined and specific genetic alterations has used homologous recombination to control the site of integration of an introduced marker gene sequence in tumor cells and in fusions between diploid human fibroblast and tetraploid mouse erythroleukemia cells (Smithies, O. et al., *Nature* 317:230–234 (1985)).

This approach was further exploited by Thomas, K. R., and co-workers, who described a general method, known as "gene targeting," for targeting mutations to a preselected, desired gene sequence of an ES cell in order to produce a transgenic animal (Mansour, S. L. et al., *Nature* 336:348–352 (1988); Capecchi, M. R., *Trends Genet.* 5:70–76 (1989); Capecchi, M. R., *Science* 244:1288–1292 (1989); Capecchi, M. R. et al., In: *Current Communications in Molecular Biology*, Capecchi, M. R. (ed.), Cold Spring Harbor Press, Cold Spring Harbor, N.Y. (1989), pp. 45–52; Frohman, M. A. et al., *Cell* 56:145–147 (1989); all of which references are incorporated herein by reference).

It may now be feasible to deliberately alter any gene in a mouse (Capecchi, M. R., *Trends Genet.* 5:70–76 (1989); Frohman, M. A. et al., *Cell* 56:145–147 (1989)). Gene targeting involves the use of standard recombinant DNA techniques to introduce a desired mutation into a cloned DNA sequence of a chosen locus. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

Gene targeting has been used to produce chimeric and transgenic mice in which an nptII gene has been inserted into the $\beta_2$-microglobulin locus (Koller, B. H. et al., *Proc. Natl. Acad. Sci. (U.S.A.)* 86:8932–8935 (1989); Zijlstra, M. et al., *Nature* 342:435–438 (1989); Zijlstra, M. et al., *Nature* 344:742–746 (1989); DeChiaba et al., *Nature* 345:78–80 (1990)). Similar experiments have enabled the production of chimeric and transgenic animals having a c-abl gene which has been disrupted by the insertion of an nptII gene (Schwartzberg, P. L. et al., *Science* 246:799–803 (1989)). The technique has been used to produce chimeric mice in which the en-2 gene has been disrupted by the insertion of an nptII gene (Joyner, A. L. et al., *Nature* 338:153–155 (1989)).

Gene targeting has also been used to correct an hprt deficiency in an hprt⁻ ES cell line. Cells corrected of the deficiency were used to produce chimeric animals. Significantly, all of the corrected cells exhibited gross disruption of the regions flanking the hprt locus; all of the cells tested were found to contain at least one copy of the vector used to correct the deficiency, integrated at the hprt locus (Thompson, S. et al., *Cell* 56:313–321 (1989); Koller, B. H. et al., *Proc. Natl. Acad. Sci. (U.S.A.)* 86:8927–8931 (1989)).

In order to utilize the "gene targeting" method, the gene of interest must have been previously cloned, and the intron-exon boundaries determined. The method results in the insertion of a marker gene (i.e. the nptII gene) into a translated region of a particular gene of interest. Thus, use of the gene targeting method results in the gross destruction of the gene of interest.

Recently, chimeric mice carrying the homeobox hox 1.1 allele have been produced using a modification of the gene targeting method (Zimmer, A. et al., *Nature* 338:150–154 (1989). In this modification, the integration of vector sequences was avoided by microinjecting ES cells with linear DNA containing only a portion of the hox 1.1 allele, without any accompanying vector sequences. The DNA was found to cause the gene conversion of the cellular hox allele. Selection was not used to facilitate the recovery of the "converted" ES cells, which were identified using the polymerase chain reaction ("PCR"). Approximately 50% of cells which had been clonally purified from "converted" cells were found to contain the introduced hox 1.1 allele, suggesting to Zimmer, A. et al. either chromosomal instability or contamination of sample. None of the chimeric mice were found to be able to transmit the "converted" gene to their progeny (Zimmer, A. et al., In: *Current Communications in Molecular Biology*, Capecchi, M. R. (ed.), Cold Spring Harbor Press, Cold Spring Harbor, N.Y. (1989), pp. 53–58).

Significantly, the use of gene targeting to alter a gene of a cell results in the formation of a gross alteration in the sequence of that gene. The efficiency of gene targeting depends upon a number of variables, and is different from construct to construct. For the p53 gene constructs used herein, such efficiency is approximately 1/300.

V. Production of Chimeric and Transgenic Animals: Use of Insertion Vectors

In contrast to the above-described methods, the present invention uses methods capable of producing subtle, precise, and predetermined mutations in the sequence of one of the two alleles of the p53 gene of a human or animal cell. Although the methods discussed below are capable of mutating both alleles of the cell's p53 gene, it is possible to readily identify (for example through the use of PCR (discussed below), or other methods) such dual mutational events. Since the frequency of such dual mutational events is the square of the frequency of a single mutational event, cells having mutations in both of their p53 alleles will be only a very small proportion of the total population of mutated cells.

The present invention has several embodiments. In the simplest embodiment, an insertion vector is used to mutate the nucleotide sequence of one of the two alleles of the p53 gene of a cell. The use of this vector type in combination with a second selectable reversion event prevents the disruption of the chromosome by the selectable marker gene (an nptII gene, for example) of the vector or by other vector sequences. Thus, gross distortions of the recipient chromosome are avoided. The efficiency of the gene targeting is substantially greater than in the gene targeting methods discussed above.

Most preferably, the DNA molecule(s) which are to be introduced into the recipient cell contains a region of homology with a region of the p53 gene. In a preferred embodiment, the DNA molecule will contain two regions of homology with the cell's p53 gene. These regions of homology will preferably flank the precise sequence whose incorporation into the p53 gene is desired. As stated above, the regions of homology may be of any size greater than two bases long. Most preferably, the regions of homology will be greater than 10 bases long.

The DNA molecule(s) may be single stranded, but are preferably double stranded. The DNA molecule(s) may be introduced to the cell as one or more RNA molecules which may be converted to DNA by reverse transcriptase or by other means. Preferably, the DNA molecule will be double stranded linear molecule. In the best mode for conducting the invention, such a molecule is obtained by cleaving a closed covalent circular molecule to form a linear molecule. Preferably, a restriction endonuclease capable of cleaving the molecule at a single site to produce either a blunt end or staggered end linear molecule is employed. Most preferably, the nucleotides on each side of this restriction site will comprise at least a portion of the preferred two regions of homology between the DNA molecule being introduced and the p53 gene.

The invention thus provides a method for altering the natural p53 gene sequence through the introduction of a "desired gene sequence" into that gene. The "desired gene sequence" may be of any length, and have any nucleotide sequence. It may comprise one or more gene sequences which encode complete proteins, fragments of such gene sequences, regulatory sequences, etc. Significantly, the desired gene sequence may differ only slightly from a native gene of the recipient cell (for example, it may contain single, or multiple base alterations, insertions or deletions relative to the native gene). The use of such desired gene sequences permits one to create subtle and precise changes in the p53 gene of the recipient cell. Thus, the present invention provides a means for manipulating and modulating the expression and regulation of the p53 gene.

In particular, the invention provides a mean for manipulating and modulating p53 gene expression and protein structure through the replacement of a naturally present p53 gene sequence with a "non-selectable" "desired gene sequence." A gene sequence is non-selectable if its presence or expression in a recipient cell provides no survival advantage to the cell under the culturing conditions employed. Thus, by definition, one cannot select for cells which have received a "non-selectable" gene sequence in their p53 gene. In contrast, a "dominant" gene sequence is one which can under certain circumstances provide a survival advantage to a recipient cell. The neomycin resistance conferred by the nptII gene is a survival advantage to a cell cultured in the presence of neomycin or G418. The nptII gene is thus a dominant, rather than a non-selectable gene sequence.

In particular, the invention permits the replacement of the naturally present p53 gene sequence of a recipient cell with an "analog" sequence. A sequence is said to be an analog of another sequence if the two sequences are substantially similar in sequence, but have minor changes in sequence corresponding to single base substitutions, deletions, or insertions with respect to one another, or if they possess "minor" multiple base alterations. Such alterations are intended to exclude insertions of dominant selectable marker genes.

When the desired gene sequence, flanked by regions of homology with the p53 gene sequence of the recipient cell, is introduced into the recipient cell as a linear double stranded molecule, whose termini correspond to the regions of homology, a single recombination event with the p53 gene of the cell will occur in approximately 5% of the transfected cells. Such a single recombinational event will lead to the integration of the entire linear molecule into the genome of the recipient cell.

The structure generated by the integration of the linear molecule will undergo a subsequent, second recombinational event (approximately $10^{-5}$–$10^{-7}$ per cell generation). This second recombinational event will result in the elimination of all DNA except for the flanking regions of homology, and the desired DNA sequence from the integrated structure. Thus, the consequence of the second recombinational event is to replace the DNA sequence which is normally present between the flanking regions of homology in the cell's p53 gene, with the desired DNA sequence, and to eliminate the instability of gene replacement.

The DNA molecule containing the desired gene sequence may be introduced into the pluripotent cell by any method which will permit the introduced molecule to undergo recombination at its regions of homology. Some methods, such as direct microinjection, or calcium phosphate transformation, may cause the introduced molecule to form concatemers upon integration. These concatemers may resolve themselves to form non-concatemeric integration structures. Since the presence of concatemers is not desired, methods which produce them are not preferred. In a preferred embodiment, the DNA is introduced by electroporation (Toneguzzo, F. et al., *Nucleic Acids Res.* 16:5515–5532 (1988); Quillet, A. et al., *J. Immunol.* 141:17–20 (1988); Machy, P. et al., *Proc. Natl. Acad. Sci. (U.S.A.)* 85:8027–8031 (1988); all of which references are incorporated herein by reference).

After permitting the introduction of the DNA molecule(s), the cells are cultured under conventional conditions, as are known in the art.

In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable marker gene sequence.

In one embodiment, the presence of the detectable marker sequence in a recipient cell is recognized by hybridization, by detection of radiolabelled nucleotides, or by other assays of detection which do not require the expression of the detectable marker sequence. Preferably, such sequences are detected using PCR (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference).

PCR achieves the amplification of a specific nucleic acid sequence using two oligonucleotide primers complementary to regions of the sequence to be amplified. Extension products incorporating the primers then become templates for subsequent replication steps. PCR provides a method for selectively increasing the concentration of a nucleic acid molecule having a particular sequence even when that molecule has not been previously purified and is present only in a single copy in a particular sample. The method can be used to amplify either single or double stranded DNA.

Most preferably, however, the detectable marker gene sequence will be expressed in the recipient cell, and will result in a selectable phenotype. Examples of such preferred detectable gene sequences include the hprt gene (Littlefield, J. W., *Science* 145:709–710 (1964), herein incorporated by reference), the tk gene (i.e. thymidine kinase gene) and especially the tk gene of herpes simplex virus (Giphart-Gassler, M. et al., *Mutat. Res.* 214:223–232 (1989) herein incorporated by reference), the nptII gene (Thomas, K. R. et al., *Cell* 51:503–512 (1987); Mansour, S. L. et al., *Nature* 336:348–352 (1988), both references herein incorporated by reference), or other genes which confer resistance to amino acid or nucleoside analogues, or antibiotics, etc.

Cells which express an active HPRT enzyme are unable to grow in the presence of certain nucleoside analogues (such as 6-thioguanine, 8-azapurine, etc.), but are able to grow in media supplemented with HAT (hypoxanthine, aminopterin, and thymidine). Conversely, cells which fail to express an active HPRT enzyme are unable to grow in media containing HATG, but are resistant to analogues such as 6-thioguanine, etc. (Littlefield, J. W., *Science* 145:709–710 (1964)). Cells expressing active thymidine kinase are able to grow in media containing HATG, but are unable to grow in media containing nucleoside analogues such as 5-azacytidine (Giphart-Gassler, M. et al., *Mutat. Res.* 214:223–232 (1989)). Cells containing an active HSV-tk gene are incapable of growing in the presence of gangcylovir or similar agents.

The detectable marker gene may be any gene which can complement for a recognizable cellular deficiency. Thus, for example, the gene for HPRT could be used as the detectable marker gene sequence when employing cells lacking HPRT activity. Thus, this agent is an example of agents may be used to select mutant cells, or to "negatively select" for cells which have regained normal function.

The nptII gene (Southern, P. J., et al., *J. Molec. Appl. Genet.* 1:327–341 (1982); Smithies, O. et al., *Nature* 317:230–234 (1985), which references are incorporated herein by reference) is the most preferred detectable marker gene sequence. Constructs which contain both an nptII gene and either a tk gene or an hprt gene are especially preferred.

A. Use of a Single DNA Molecule Containing Both the Detectable Marker Sequence and the Desired Gene Sequence In a first preferred embodiment, the detectable marker gene sequence, flanked by the regions of homology to the p53 gene, is provided to the recipient cells on the same DNA molecule which contains the desired gene sequence. As discussed previously, it is preferred that this DNA molecule be a linear molecule.

After selection for cells which have incorporated the desired DNA molecule (for example by selection for G418 resistant cells when the detectable marker gene sequence is an expressible nptII gene sequence), the cells are cultured, and the presence of the introduced DNA molecule is confirmed as described above. Approximately $10^7$ cells are cultured and screened for cells which have undergone the second recombinational event (discussed above) resulting in the replacement of a native sequence (i.e. a gene sequence which is normally and naturally present in the recipient cell) with the desired gene sequence.

Any of a variety of methods may be used to identify cells which have undergone the second recombinational event. Direct screening of clones, use of PCR, use of hybridization probes, etc., may all be employed for this purpose. In a preferred embodiment, the DNA molecule will, in addition to the desired gene sequence, the flanking regions of homology and the detectable marker gene sequence, contain an additional gene sequence which will permit the selection or recognition of cells which have undergone the second recombinational event. This additional gene sequence will be excised from the cell's p53 gene as a direct consequence of the second recombinational event. Thus, gene sequences which are suitable for this purpose include any gene sequence whose loss from a cell can be detected or selected for. Examples of such "negative selection" gene sequences include the hprt gene, and the tk gene (especially the tk gene of herpes simplex virus).

In the first preferred embodiment, the frequency of the second recombinational event is approximately $10^{-5}$. However, the use of a "negative selection" gene sequence permits one to identify such recombinant cells at a frequency of approximately 100%.

The DNA molecule may have a region of heterology located at the proposed insertion site. Insertion of such a vector permits one to select for recombinants which have recombined at the insertion site (and not at other potential sites). If recombination occurs at the desired insertion site, it will lead to the loss of the sequence of heterology located at the proposed insertion site of the DNA molecule (HSVtk, for example). Insertions which result from other recombinational events will retain the sequence of heterology. Thus, by employing a region of heterology which encodes an assayable gene product, or which can be used as a "negative selectable" marker, one can readily determine that the locus of insertion of the recipient cell contains the precise sequence desired. The efficiency of such a vector is approximately 0.5%.

The region of heterology which may be introduced at the insertion site of the DNA molecule may be either short or of substantial size (for example, 2 kb). The site of linearization may be 5', 3', or within the region of heterology. When the site of linearization is within the region of heterology, the efficiency of gene targeting is approximately 2%.

The region of heterology may be located at a site internal to the region of homology where the desired recombination shall occur. Such a construct can be used when one desires to introduce a subtle mutation into a locus of the cellular gene at a site other than that of the site of desired recombination.

B. Use of a Different DNA Molecules to Provide the Detectable Marker Sequence and the Desired Gene Sequence In a second preferred embodiment, the detectable marker gene sequence, flanked by the regions of homology, will be provided to the recipient cell on a different DNA molecule from that which contains the desired gene sequence. It is preferred that these molecules be linear molecules.

When provided on separate DNA molecules, the detectable marker gene sequence and the desired gene sequence will most preferably be provided to the recipient cell by co-electroporation, or by other equivalent techniques.

After selection of such recipients (preferably through the use of a detectable marker sequence which expresses the nptII gene and thus confers cellular resistance to the antibiotic G418), the cells are grown up and screened to confirm the insertion event (preferably using PCR).

In the absence of any selection, only one cell in $10^7$ would be expected to have the predicted recombinant structures. If, however, one selects for recipient cells which contain and express a detectable marker sequence (such as the nptII gene), it is possible to obtain a $10^3$ to $10^5$ fold enrichment for cells which have taken up both DNA molecules. Typically, such enrichment enables one to identify the desired recipient cell (in which the introduced DNA has integrated into the cell's genome) by screening only 800–1,500 cells. Such screening is preferably done using PCR, or other equivalent methods. Using such negative selection techniques, one may manipulate the vector copy number.

The two introduced DNA molecules will generally not have integrated into the same site in the genome of the recipient cell. Thus, in some cases, the desired gene sequence will have integrated in a manner so as to replace the native cellular gene sequence between the flanking regions of homology. The locus of integration of the detectable marker gene is unimportant for the purposes of the present invention, provided it is not genetically linked to the locus of the p53 gene. If desired, however, it is possible to incorporate a gene sequence capable of negative selection along with the DNA containing the detectable marker sequence. Thus, one can ultimately select for cells which have lost the introduced selectable marker gene sequence DNA.

C. Use of Direct Selection to Identify Homologous Recombination Events

Although all of the above-described preferred embodiments enable the isolation of cells in which one of the cell's p53 alleles has been mutated to contain a desired gene sequence, each embodiment requires the screening of a significant number of candidate cells in order to identify the desired recombinant cell. It is, however, possible to directly select for the desired recombinant cell by employing a variation of the above embodiments.

The method for direct selection of the desired cells relies upon the phenotypic difference in targeted and non-targeted cells and the use of a single gene which can be used for both positive and negative selection.

Typically, in any homologous recombination experiment performed with an insertion vector, three populations of cells will be created. The first class of cells will be those which have failed to receive the desired DNA molecule. This class will comprise virtually all of the candidate cells isolated on completion of the experiment. The second class of cells will be those cells in which the desired gene sequence has been incorporated at a random insertion site (i.e. a site other than in the p53 gene). Approximately one cell in $10^3$–$10^4$ total cells will be in this class. The third class of cells will be those cells in which the desired gene sequence has been incorporated by homologous recombination into a site in the p53 gene. Approximately one cell in $10^5$–$10^6$ total cells will be in this class.

In the above-described embodiments, the cells of the first class (non-transfected cells) can be eliminated by positive selection, thus necessitating the screening of only about 1,000 cells in order to identify the desired recombinant cell. In the present embodiment, cells of the third class (homologous recombinants) may be selected from the cells of the second class (random insertions) if a phenotypic difference exists between the cells of the two classes.

Since random integration sites are likely to be concatemeric with few single copy clones (depending upon the DNA concentration with which the cells were transfected), such integration events are inherently unstable. Thus, such concatemeric constructs will typically undergo intrachromosomal recombination. Such recombination will always leave one intact copy of the vector in the genome. Thus, all random insertion events may be negatively selected from the population if a negatively selectable marker is included on the vector.

In contrast, cells in which the desired gene sequence has been incorporated into the p53 gene by homologous recombination will revert with a relatively high frequency (approximately 1 in $10^4$–$10^5$ per cell division (depending upon the size of the duplicated structure) to produce a mutated p53 gene that does not contain vector sequences. Therefore, even if the vector contained a negatively selectable gene sequence, such cells will survive negative selection, and can be recovered. The small percentage of homologous recombinant cells which have not undergone reversion will also be eliminated by the negative selection.

A preferred negative selectable marker is the hprt gene (cells expressing an active HPRT enzyme are unable to grow in the presence of certain nucleoside analogues such as 6-thioguanine, etc.). When using 6-thioguanidine as a negative selection agent, a density of $10^7$ cells is preferably used since the efficiency of 6-thioguanidine selection is cell density dependent. A typical experiment with $10^7$ transfected cells would yield approximately 10 revertant cells after successive selection. The relative yield of revertant clones can be substantially increased by using "Poly A Selection" for the first round of selection.

In such a "Poly A Selection" one exploits the fact that, if an introduced DNA molecule were to integrate at random into the host chromosome, it would generally not integrate at a site adjacent to a necessary 3' polyadenylation site. Thus, the mRNA produced by the transcription of such randomly inserted constructs would generally lack polyadenylation. This fact can be exploited by using vectors which permit one to select for a recombinational event that results in integration adjacent to the natural polyadenylation site of the introduced gene sequence (i.e. by homologous recombination rather than by random insertion). As stated above, the frequency of obtaining a desired recombinant cell is approximately $10^{-3}$. By using Poly A Selection, desired cells can be recovered at a frequency of approximately $10^{-2}$. Thus, the poly A selection results in an approximate increase of overall efficiency of nearly 10 fold. Poly A selection may therefore be advantageously used in situations where one desires to minimize or avoid the screening of colonies to identify random versus homologous recombinants.

D. Production of Altered p53 Alleles Containing Heterologous Sequences

As stated above, the desired gene sequence may be of any length, and have any nucleotide sequence. In particular, it is possible to design the sequence of the desired gene sequence in order to create single, or multiple base alterations, insertions or deletions in any preselected gene of a cell.

If such changes are within a translated region of the p53 gene sequence, then a new protein variant of the p53 gene product can be obtained.

The present invention may be used to produce cells in which the natural p53 gene has been replaced with an altered gene sequence, or a heterologous p53 gene. A p53 gene is said to be heterologous to a transgenic cell if it is derivable from a species other than that of the transgenic cell.

In one embodiment, this replacement may be accomplished in a single step. To accomplish such replacement, a DNA molecule containing a desired gene sequence and a region of homology with the p53 gene is introduced into a recipient cell. A selectable marker gene is also introduced into the cell, and used to select for cells which have underwent recombination. The method results in the replacement of the normal sequences adjacent to the region of homology with the heterologous sequences of the desired DNA sequence.

In a second embodiment, this replacement may be accomplished in two steps. As in the embodiment described above, a cell is provided with a DNA molecule containing a desired gene sequence and a region of homology with the p53 gene. The DNA molecule also contains a selectable marker gene used to select for cells which have undergone a recombinational event that has resulted in the insertion of the introduced DNA molecule into their chromosomes at the site of homology.

Significantly, in this embodiment, the introduced DNA molecule will also contain a "negative selectable" marker gene which can be used to select for cells which undergo a second recombinational event that results in the loss of the inserted DNA.

A second DNA molecule is employed to complete the gene replacement. This second DNA molecule need not contain any selectable marker gene. Upon receipt of the second DNA molecule, a second recombinational event occurs which exchanges the "second" DNA molecule for the integrated "first" DNA molecule (including the desired DNA sequence, the selectable marker sequence, and the "negative selectable" marker sequence contained on that molecule).

In another embodiment of the invention, subtle mutations may be introduced into a desired locus using a "cassette" construct containing both a positive selection marker (such as the nptII gene or the gpt gene) and a negative selection marker (such as the tk gene). In this embodiment, one first uses the positive selection capacity of the construct to introduce the two selection markers into a desired locus. One then introduces the desired subtle mutations (substitutions, insertions, deletions, etc.) by providing a cell with a DNA molecule that contains the desired mutation. By selecting for the loss of the "cassette" (using the negative selection marker), one can select for recombinational events which result in the replacement of the "cassette" sequence with the DNA sequence containing the desired mutation.

The present invention may also be used to replace contiguous regions of a chromosome with any desired gene sequence. Thus, the present invention is not limited in the size of the DNA regions which may be altered or replaced. This aspect of the present invention may be considered as a series of 5 steps. The first step in replacing a large region of a chromosome with a desired sequence involves setting up an initial target. In this step, a recipient cell is provided with a DNA molecule which contains a "first fragment" of the total desired replacement sequence. This "first fragment" of the desired replacement sequence contains a selectable marker sequence (most preferably the nptII gene) at its end.

The DNA molecule also contains a "dual selection" gene sequence which encodes a non-functional fragment of a gene sequence for which both a positive and a negative selection exists. An example of such a gene is the gpt gene when used in the context of an hprt⁻ cell. Cells which express a functional gpt gene can be selected for by their ability to grow in HAT medium; Cells which lack a functional gpt gene can be selected for by their ability to grow in the presence of 6-thioguanine.

Homologous recombination results in the insertion of the DNA molecule into the cell's genome at the region of homology. Importantly, since this step results in the creation of a cell whose genome contains the selectable marker gene, it is possible to select for the desired recombinational event.

In the second step of the method, a second DNA molecule is provided to the cell. This second DNA molecule contains a "second fragment" of the desired replacement sequence as well as a sequence of the dual selection gene that, due to an internal deletion, is incapable of encoding a functional gene product. Homologous recombination results in the insertion of the second DNA molecule into the cell's genome in a manner so as to create a functional dual selection gene. Recombination also results in the integration of a non-functional fragment of the dual selection gene. Importantly, since this step results in the creation of a cell whose genome contains a functional dual selection gene, it is possible to select for the desired recombinational event.

In the third step of the method, a third DNA molecule is provided to the cell. This third DNA molecule contains both the "first" and "second" fragments of the desired replacement sequence. Homologous recombination results in the insertion of the third DNA molecule into the cell's genome in a manner so as to delete the functional dual selection gene. The non-functional fragment of the dual selection gene (formed in step 2) is not affected by the recombination, and is retained. Importantly, since this step results in the creation of a cell whose genome lacks the dual selection gene, it is possible to select for the desired recombinational event.

In the fourth step of the method, a fourth DNA molecule is provided to the cell. This fourth DNA molecule contains a "third fragment" of the desired replacement sequence as well as a sequence of the dual selection gene that, as in step 2, is incapable of encoding a functional gene product due to an internal deletion. Homologous recombination results in the insertion of the fourth DNA molecule into the cell's genome in a manner so as to create a functional dual selection gene. Recombination also results in the integration of a non-functional fragment of the dual selection gene. Importantly, since this step results in the creation of a cell whose genome contains a functional dual selection gene, it is possible to select for the desired recombinational event.

In the fifth step of the method, a fifth DNA molecule is provided to the cell. This fifth DNA molecule contains both the "second" and "third" fragments of the desired replacement sequence. Homologous recombination results in the insertion of the fifth DNA molecule into the cell's genome in a manner so as to delete the functional dual selection gene. The non-functional fragment of the dual selection gene (formed in step 4) is not affected by the recombination, and is retained. Importantly, since this step results in the creation of a cell whose genome lacks the dual selection gene, it is possible to select for the desired recombinational event.

As will be appreciated, the net effect of the above-described steps is to produce a cell whose genome has been engineered to contain a "first," "second," and "third" "fragment" of a particular desired gene in a contiguous manner. The steps may be repeated as desired in order to introduce additional "fragments" into the cell's genome. In this manner, cells can be constructed which contain heterologous genes, chromosome fragments, or chromosomes, that could not be introduced using a single vector. As indicated above, it is possible to select for each step of the method.

VI. The Production of Chimeric and Transgenic Animals

The chimeric or transgenic animal cells of the present invention are prepared by introducing one or more DNA molecules into a precursor pluripotent cell, most preferably an ES cell, or equivalent (Robertson, E. J., In: *Current Communications in Molecular Biology*, Capecchi, M. R. (ed.), Cold Spring Harbor Press, Cold Spring Harbor, N.Y. (1989), pp. 39–44, which reference is incorporated herein by reference). The term "precursor" is intended to denote only that the pluripotent cell is a precursor to the desired ("transfected") pluripotent cell which is prepared in accordance with the teachings of the present invention. The pluripotent (precursor or transfected) cell may be cultured in vivo, in a manner known in the art (Evans, M. J. et al., *Nature* 292:154–156 (1981)) to form a chimeric or transgenic animal.

Any ES cell may be used in accordance with the present invention. It is, however, preferred to use primary isolates of ES cells. Such isolates may be obtained directly from embryos such as the CCE cell line disclosed by Robertson, E. J., In: *Current Communications in Molecular Biology*, Capecchi, M. R. (ed.), Cold Spring Harbor Press, Cold Spring Harbor, N.Y. (1989), pp. 39–44), or from the clonal isolation of ES cells from the CCE cell line (Schwartzberg, P. A. et al., *Science* 246:799–803 (1989), which reference is incorporated herein by reference). Such clonal isolation may be accomplished according to the method of E. J. Robertson (In: *Teratocarcinomas and Embryonic Stem Cells: A Practical Approach*, (E. J. Robertson, Ed.), IRL Press, Oxford, 1987) which reference and method are incorporated herein by reference. The purpose of such clonal propagation is to obtain ES cells which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage. An example of ES cell lines which have been clonally derived from embryos are the ES cell lines, AB1 ($hprt^+$) or AB2.1 ($hprt^-$).

The ES cells are preferably cultured on stromal cells (such as STO cells (especially SNC4 STO cells) and/or primary embryonic fibroblast cells) as described by E. J. Robertson (In: *Teratocarcinomas and Embryonic Stem Cells: A Practical Approach*, (E. J. Robertson, Ed.), IRL Press, Oxford, 1987, pp 71–112), which reference is incorporated herein by reference. Methods for the production and analysis of chimeric mice are disclosed by Bradley, A. (In: *Teratocarcinomas and Embryonic Stem Cells: A Practical Approach*, (E. J. Robertson, Ed.), IRL Press, Oxford, 1987, pp 113–151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough, N. M. et al., *Reprod. Fertil. Dev.* 1:281–288 (1989); Yamamori, Y. et al., *Science* 246:1412–1416 (1989), both of which references are incorporated herein by reference). Since the gene encoding lif has been cloned (Gough, N. M. et al., *Reprod. Fertil. Dev.* 1:281–288 (1989)), it is especially preferred to transform stromal cells with this gene, by means known in the art, and to then culture the ES cells on transformed stromal cells that secrete lif into the culture medium.

ES cell lines may be derived or isolated from any species (for example, chicken, etc.), although cells derived or isolated from mammals such as rodents (i.e. mouse, rat, hamster, etc.), rabbits, sheep, goats, fish, pigs, cattle, primates and humans are preferred.

VII. Uses of the Present Invention

The present invention provides human or animal cells which contain a desired gene sequence in one of the two p53 alleles of the cell's genome.

In a first embodiment, the invention also provides a means for producing non-human chimeric or transgenic animals whose cells contain such a sequence. The animals which may be produced through application of the described method include chicken, non-human mammals (especially, rodents (i.e. mouse, rat, hamster, etc.), rabbits, sheep, goats, fish, pigs, cattle and non-human primates).

The cells and non-human animals of the present invention have both diagnostic and therapeutic utility.

A. Diagnostic Utility

Since the invention provides a cell, or a transgenic or chimeric non-human animal that contains a single functional allele of the p53 gene, and since such cells will become tumor cells upon the mutation of the functional allele to a non-functional form, the present invention can be used to identify an agent that is capable of affecting a characteristic of an animal cell that is attributable to the presence or expression of a tumor-suppressing gene. A characteristic of an animal cell is said to be "attributable to the presence or expression of a tumor-suppressing gene," if the characteristic is altered by the absence or lack of expression of the tumor-suppressing gene. Examples of such characteristics include tumorigenesis, resilience to tumorigenesis, the extent, distribution, incidence, location, grade, etc. of tumors, etc.

In one embodiment, such agents can decrease the tumorigenic (or neoplastic) potential of the cells or animals. Such agents are discussed below with regard to the therapeutic potential of the invention.

In a second embodiment, such agent can increase the tumorigenic (or neoplastic) potential of the cells or animals. Thus, the cells and non-human animals of the present invention have utility in testing potential or suspected carcinogens for tumorigenic activity. They may be used to identify and assess the tumorigenic effects of agents that may be present, for example, in the environment (such as environmental pollutants in air, water or soil), or resulting from environmental exposures to chemicals, radioisotopes, etc. They may also be used to facilitate studies of the effects of diet on oncogenesis. They may be used to determine whether potential or present food additives, chemical waste products, chemical process by-products, water sources, proposed or presently used pharmaceuticals, cosmetics, etc., have tumorigenic activity. They may also be used to determine the tumorigenic potential of various energy forms (such as UV rays, X-rays, ionizing radiation, gamma rays of elemental isotopes, etc.).

The frequency at which a mutational event occurs is dependent upon the concentration of a mutagenic chemical agent, or the intensity of a mutagenic radiation. Thus, since the frequency of a single cell receiving two mutational events is the square of the frequency at which a single mutational event will occur, the cells and non-human animals of the present invention shall be able to identify neoplastic (mutagenic) agents at concentrations far below those needed to induce neoplastic changes in natural cells or animals.

One especially preferred cell is a non-human cell in which one of the natural p53 alleles has been replaced with a functional human p53 allele and the other of the natural p53 alleles has been mutated to a non-functional form. Alternatively, one may employ a non-human cell in which the two natural p53 alleles have been replaced with a functional and a non-functional allele of the human p53 gene.

Such cells may be used, in accordance with the methods described above to assess the neoplastic potential of agents in cells containing the human p53 allele. More preferably, such cells are used to produce non-human animals which do not contain any natural functional p53 alleles, but which contain only one functional human p53 allele. Such non-human animals can be used to assess the tumorigenicity of an agent in a non-human animal expressing the human p53 gene product.

1. In Vitro Assays

In one embodiment, one may employ the cells of the present invention, in in vitro cell culture, and incubate such cells in the presence of an amount of the agent whose tumorigenic potential is to be measured. This embodiment therefore comprises an in vitro assay of tumorigenic activity.

Although many carcinogenic agents may directly mediate their tumorigenic effects, some agents will not exhibit tumorigenic potential until metabolized, or until presented to a susceptible cell along with one or more "co-carcinogenic" factors. The present invention permits the identification of such "latent" carcinogenic and "co-carcinogenic" agents. In accordance with this embodiment of the invention, the presence of a "latent" carcinogen can be identified by merely maintaining cell or animal exposure to a candidate agent. Alternatively, the cells of the present invention can be incubated in "spent" culture medium (i.e. medium containing the candidate agent that was used to culture other cells before being used to culture the cells of the present invention).

The present invention permits the identification of co-carcinogenic factors capable of inducing neoplastic effects in the presence of a second agent. Such factors can be identified by culturing the cells of the present invention in the presence of two or more candidate agents simultaneously, and then assaying for neoplasia.

The transformation of the cells to a neoplastic state would be indicative of tumorigenic (or neoplastic) activity of the assayed agent. Such a neoplastic state may be evidenced by a change in cellular morphology, by a loss of contact inhibition, by the acquisition of the capacity to grow in soft agar, or most preferably, by the initiation of expression of tumor antigens.

The use of tumor antigens as a means of detecting neoplastic activity is preferred since such antigens may be readily detected.

As is well known in the art, antibodies, or fragments of antibodies, may be used to quantitatively or qualitatively detect the presence tumor of antigens on cell surfaces. Since any cell type (i.e. lung, kidney, colon, etc.) may be employed to form the p53-mutated cells of the present invention, it is possible to determine whether an agent has a tissue specific tumorigenic potential. To accomplish this goal, one would incubate a candidate agent in the presence of p53-mutated cells derived from any of a variety of tissue types. Since tumors have tumor-specific antigens, and since antibodies capable of binding to such antigens have been isolated, it is possible to use such antibodies to characterize any tumor antigens which may be expressed by the p53-mutated cells.

Such detection may be accomplished using any of a variety of immunoassays. For example, by radioactively labeling the antibodies or antibody fragments, it is possible to detect the antigen through the use of radioimmune assays. A good description of a radioimmune assay (RIA) may be found in *Laboratory Techniques and Biochemistry in Molecular Biology*, by Work, T. S., et al., North Holland Publishing Company, NY (1978), with particular reference to the chapter entitled "An Introduction to Radioimmune Assay and Related Techniques" by Chard, T., incorporated by reference herein. Examples of suitable radioisotopic labels include $^3H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc.

Alternatively, enzyme labels, non-radioactive isotopic labels, fluorescent labels, chemiluminescent labels or other suitable labels can be employed.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable non-radioactive isotopic labels include $^{157}Gd$, $^{55}Mn$, $^{162}Dy$, $^{52}Tr$, $^{56}Fe$, etc.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The above-described in vitro assay has the advantageous features of potentially lower cost than presently used assays, and the capacity to readily screen large numbers of agents. Use of this embodiment facilitates comparisons of test results obtained at different times and conditions. Moreover, because it is possible to use very large numbers of cells in such assays, it is possible to detect the tumorigenic activity of tumorigenic agents even at very low concentrations. Lastly, since this embodiment can be performed using human cells, it provides a means for determining the tumorigenic (or neoplastic) potential of a test compound on human cells.

2. In Vivo Assays

In a second embodiment, one may employ the non-human animals of the present invention, and provide to such animals (by, for example, inhalation, ingestion, injection, implantation, etc.) an amount of the agent whose tumorigenic potential is to be measured. The formation of tumors in such animals (as evidenced by direct visualization by eye, or by biopsy, imaging, detection of tumor antigens, etc.) would be indicative of tumorigenic activity of the assayed agent.

The use of the non-human animals of the present invention is preferred over naturally occurring non-human animals since such natural animals contain two functional p53 alleles, and thus require two mutational events in order to lead to loss of functional p53 activity. In contrast, since the non-human animals of the present invention have only one functional p53 allele, only one mutational event is needed to cause total loss of p53 function.

The detection of tumors in such animals can be accomplished by biopsy, imaging, or by assaying the animals for the presence of cells which express tumor antigens.

For example, such detection may be accomplished by removing a sample of tissue from a subject and then treating the isolated sample with any suitably labeled antibodies (or antibody fragments) as discussed above. Preferably, such in situ detection is accomplished by removing a histological specimen from the subject, and providing the labeled antibody to such specimen. The antibody (or fragment) is preferably provided by applying or by overlaying the labeled antibody (or fragment) to a sample of tissue. Through the use of such a procedure, it is possible to determine not only the presence of antigen, but also the distribution of the antigen on the examined tissue. Using the present invention, those of ordinary skill will readily perceive that any of a wide variety of histological methods (such as staining procedures) can be modified in order to achieve such in situ detection.

Alternatively, the detection of tumor cells may be accomplished by in vivo imaging techniques, in which the labeled antibodies (or fragments thereof) are provided to the subject, and the presence of the tumor is detected without the prior removal of any tissue sample. Such in vivo detection procedures have the advantage of being less invasive than other detection methods, and are, moreover, capable of detecting the presence of antigen-expressing cells in tissue which cannot be easily removed from the patient.

Additionally, it is possible to assay for the presence of tumor antigens in body fluids (such as blood, lymph, etc.), stools, or cellular extracts. In such immunoassays, the antibodies (or antibody fragments) may be utilized in liquid phase or bound to a solid-phase carrier, as described below.

The use of an in vivo assay has several advantageous features. The in vivo assay permits one not only to identify tumorigenic agents, but also to assess the kind(s) of tumors induced by the agent, the number and location (i.e. whether organ or tissue specific) of any elicited tumors, and the grade (clinical significance) of such elicited tumors. It further permits an assessment of tumorigenicity which inherently considers the possible natural metabolism of the introduced agent, the possibility that the introduced agent (or its metabolic by-products) might selectively accumulate in specific tissues or organs of the recipient animal, the possibility that the recipient animal might recognize and repair or prevent tumor formation. In short, such an assay provides a true biological model for studying and evaluating the tumorigenic potential of an agent in a living non-human animal.

3. Immunoassays of Tumor Antigens

The in vitro, in situ, or in vivo detection of tumor antigens using antibodies (or fragments of antibodies) can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The binding molecules of the present invention may also be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, lymph, liquified stools, tissue homogenate, etc.) and a quantity of detectably labeled soluble antibody is added to permit detection and/or quantitation of the ternary complex formed between solid-phase antibody, antigen, and labeled antibody.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199–206 of *Radioimmune Assay Method*, edited by Kirkham and Hunter, E. & S. Livingstone, Edinburgh, 1970.

In another type of "sandwich" assay, which may also be useful to identify tumor antigens, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

As explained above, the immunometric assays for antigen require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

B. Therapeutic Utility

Significantly, the cells and animals of the present invention can be used to identify agents that decrease the tumorigenic (or neoplastic) potential of the cells or animals. Such agents can be "anti-tumor agents" and/or "chemopreventative agents." "Anti-tumor agents" act to decrease the proliferation of the cells (or the growth, dissemination, or metastasis of tumors in the chimeric or transgenic animals). "Chemopreventative agents" act to inhibit the formation of new tumors. Such agents may have general activity (inhibiting all new tumor formation), or may have a specific activity inhibiting the distribution, frequency, grade, etc.) of specific types of tumors in specific organs and tissue. Thus, the present invention permits the identification of novel antineoplastic therapeutics. Any of the above assays of tumor-suppressing activity may be used for this purpose.

The transgenic cells and non-human animals of the present invention can be used to study human gene regulation of the p53 gene. For example, such cells and animals can be used to investigate the interactions of the p53 gene with oncogenes or other tumor suppressor genes. Thus, they may be used to identify therapeutic agents which have the ability to impair or prevent neoplastic or tumorigenic development. Such agents have utility in the treatment and cure of cancer in humans and animals.

Significantly, potential therapeutic agents are frequently found to induce toxic effects in one animal model but not in another animal model. To resolve the potential of such agents, it is often necessary to determine the metabolic patterns in various species, and to then determine the toxicities of the metabolites. The present invention permits one to produce transgenic cells or animals which could facilitate such determinations.

When providing the therapeutic agents of the present invention to the cells of an animal, pharmaceutically acceptable carriers (i.e. liposomes, etc.) are preferably employed. Such agents can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Nicolau, C. et al. (*Crit. Rev. Ther. Drug Carrier Syst.* 6:239–271 (1989)), which reference is incorporated herein by reference.

In order to form a pharmaceutically acceptable composition suitable for effective administration, such compositions will contain an effective amount of the desired gene sequence together with a suitable amount of carrier vehicle.

Additional pharmaceutical methods may be employed to control the duration of action. Control release preparations may be achieved through the use of polymers to complex or absorb the desired gene sequence (either with or without any associated carrier). The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the agent into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions.

C. Use in Research and in Gene Therapy

The cells and non-human animals of the present invention, quite apart from their uses in veterinary and human medicine, may be used to investigate gene regulation, expression and organization in animals. The methods of the present invention may be used to produce alterations in a regulatory region for the native p53 gene sequence. Thus, the invention provides a means for altering the nature or control of transcription or translation of the p53 gene, and of altering the p53 gene itself. For example, the invention enables one to introduce mutations which result in increased or decreased gene expression. Similarly, it enables one to impair or enhance the transcriptional capacity of the natural p53 gene in order to decrease or increase its expression. Thus, the present invention permits the manipulation and dissection of the p53 gene.

Such abilities are especially valuable in gene therapy protocols, and in the development of improved animal models of cancer.

In one embodiment of the present invention, DNA encoding either a functional p53 gene, variants of that gene, or other genes which influence the activity of the p53 gene, may be introduced into the somatic cells of an animal (particularly mammals including humans) in order to provide a treatment for cancer (i.e. "gene therapy"). Most preferably, viral or retroviral vectors are employed for this purpose.

The principles of gene therapy are disclosed by Oldham, R. K. (In: *Principles of Biotherapy*, Raven Press, N.Y., 1987), and similar texts. Disclosures of the methods and uses for gene therapy are provided by Boggs, S. S. (*Int. J. Cell Clon.* 8:80–96 (1990)); Karson, E. M. (*Biol. Reprod.* 42:39–49 (1990)); Ledley, F. D., In: *Biotechnology, A Comprehensive Treatise, volume 7B, Gene Technology*, VCH Publishers, Inc. NY, pp 399–458 (1989)); all of which references are incorporated herein by reference.

Although, as indicated above, such gene therapy can be provided to a recipient in order to treat (i.e. suppress, attenuate, or cause regression) an existing neoplastic state, the principles of the present invention can be used to provide a prophylactic gene therapy to individuals who, due to inherited genetic mutations, or somatic cell mutation, contain cells having impaired p53 gene expression (for example, only a single functional allele of the p53 gene). Such therapy would be administered in advance of the detection of cancer in order to lessen the individual's predisposition to the disease.

Having now generally described the invention, the same will be more readily understood through reference to the following examples which are provided by way of illustration, and are not intended to be limiting of the present invention, unless specified.

EXAMPLE 1

Inactivation of the p53 Tumor Suppressor Gene in the Mouse: Overview of the Experiment Structural alterations of the p53 tumor suppressor gene have been associated with a wide array of human cancers. To examine the role of p53 in tumorigenesis and mammalian development, embryonic stems (ES) cell lines were generated in which one of the two endogenous p53 alleles has been inactivated by the insertion of a neo$^R$ gene (eg. the nptII gene of tn5) following homologous recombination.

Figure 3A:
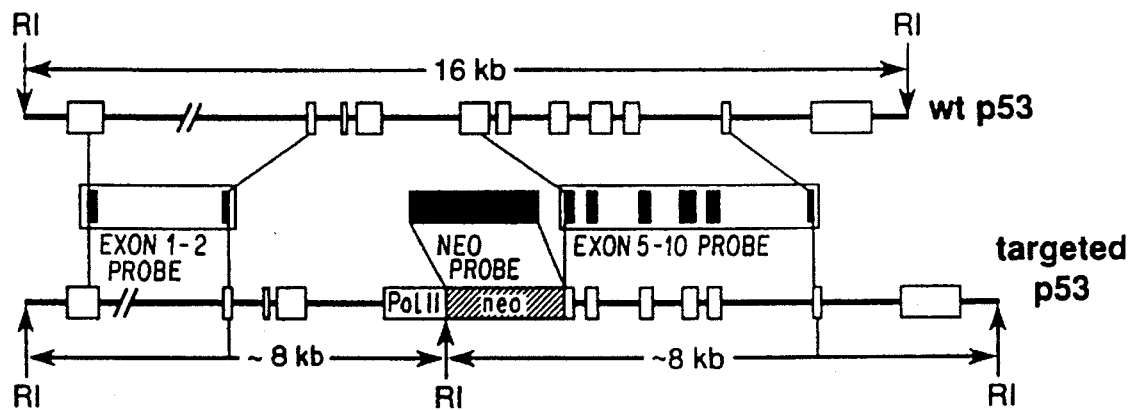
FIGS. 3(A–B) shows a comparison Southern blot of the p53 alleles present in two of the constructed embryonic stem cells (designated 1 and 2) and in wild type (wt) cells.
Figure 3B:
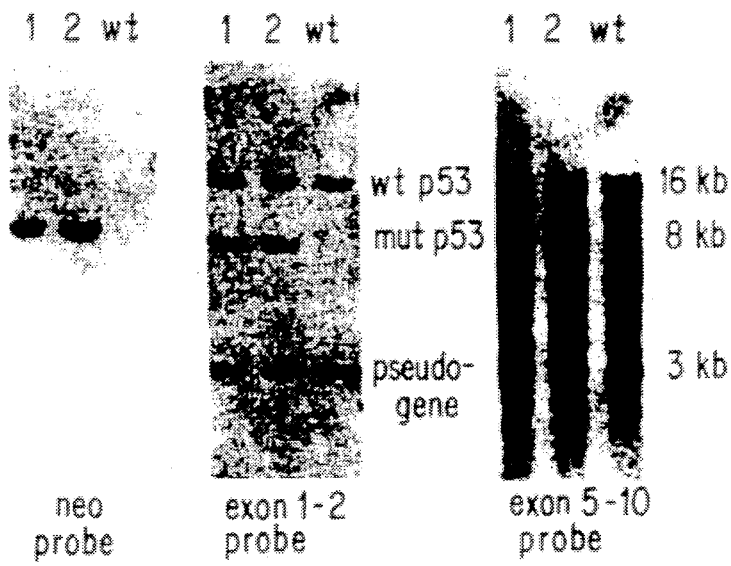

The gene targeting strategy utilized a murine p53 3.7 kb genomic construct flanked by an HSV TK gene and interrupted in exon 5 by a polyA - neo$^R$ gene driven by a pol II promoter. The 3.7 kb fragment is derived from a genomic plasmid clone of murine p53 (Oren, M. et al., *EMBO J.* 2:1633–1639 (1983); Pinhasi et al. *Molec. Cell. Biol.* 4:2180–2186 (1984)). The DNA was cloned from a liver cell of a normal Balb/c mouse. Following gene transfer into ES cells and G418/FIAU selection (as described above), two clones were identified by PCR and Southern analysis which have the expected altered p53 gene structure (FIG. 3). Three probes were used for this purpose. The first probe (neo probe) indicates the presence of the neomycin resistance determinant in the stem cells. The second and third probes (exon 1–2 and exon 5–10 probes) reveal that the wild type and mutant alleles are present in the two embryonic stem cells, but that the mutant allele is not present in the wild type (wt) cell. The fact that the three probes identify the same bands in the mutant embryonic stem cells indicates that, as expected, the neo determinant in these cells is linked to the p53 gene.

One of the heterozygous ES clones was injected into C57BL/6 recipient blastocysts and implanted into pseudopregnant C57BL/6 female mice. This ES clone was designated ESΔp53.

Embryonic stem cell line ESΔp53, (containing the p53 targeting construct of FIG. 2, as verified in FIG. 3) was deposited with the American Type Culture Collection, Rockville, Md. on Dec. 27, 1990 and was accorded the ATCC accession number: CRL 10631.

The offspring resulting from the injection of the above-described ES cell into a blastocyst, and the implantation of the blastocyst into a mouse uterus, were highly chimeric. As discussed below, the chimeric males have been bred, and germ line heterozygotes have been generated. These heterozygotes are then examined for increased tumor susceptibility and bred to determine the effects of a p53 nullizygous state on embryonic development.

EXAMPLE 2

The Generation of the Recombinogenic p53 Constructs

To maximize an ability to obtain and select ES cells containing homologous recombination events, the strategy of Mansour et al. was utilized (Mansour, S. L. et al., *Nature* 336:348–352 (1988), herein incorporated by reference). The procedure used a positive selection method for isolating cells that had stably integrated the introduced mutating DNA and a negative selection against cells that did not contain a homologous recombination event, allowing an enrichment for cells containing the desired homologous recombination event. The adaptation of these procedures for obtaining homologous recombination into the p53 gene is outlined in FIG. 1.

Figure 2:
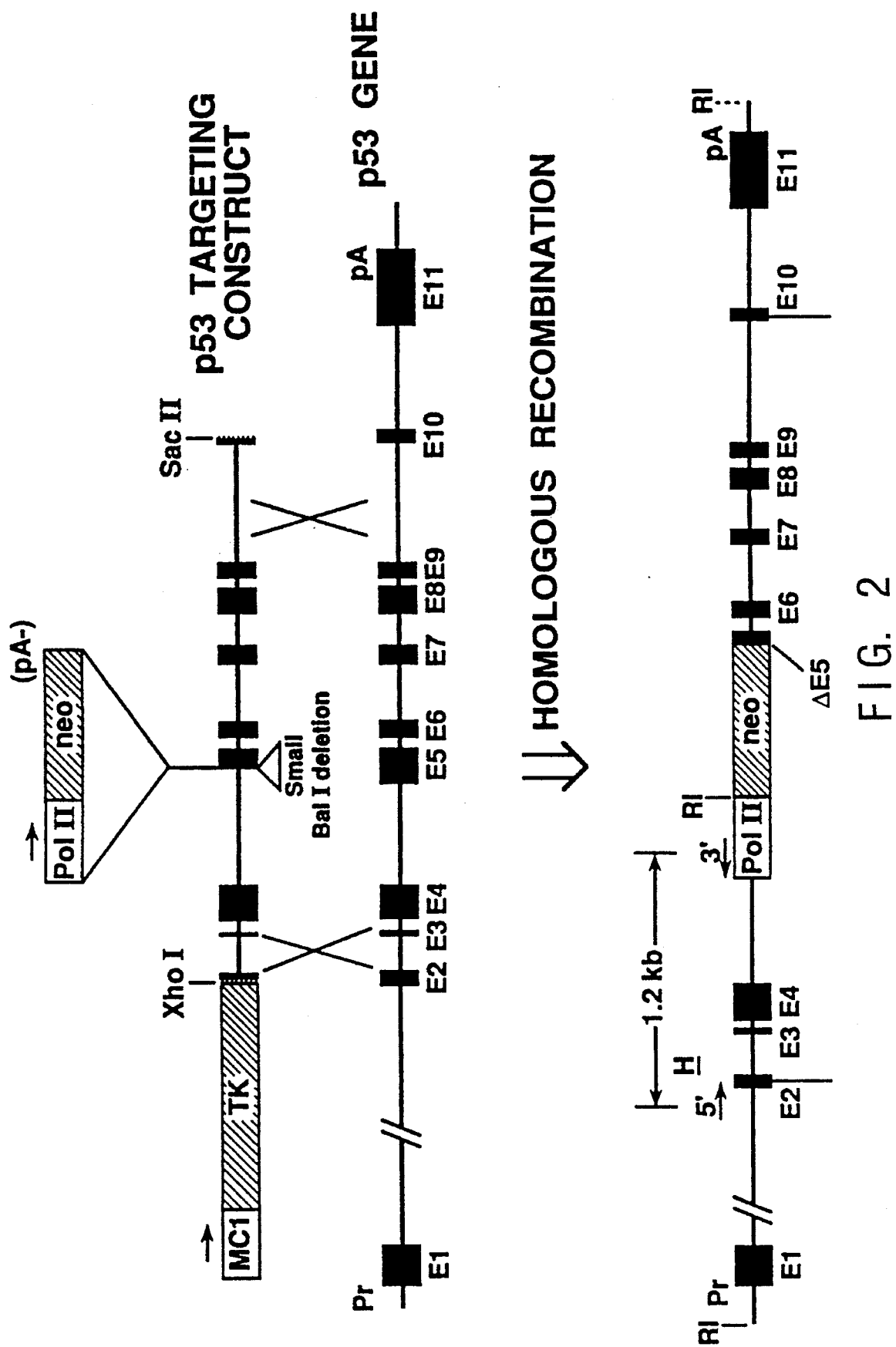
FIG. 2 shows the structure of the targeting construct used to successfully inactivate the p53 gene in mouse embryonic stem cells. The arrows labelled 5' and 3' represent the oligonucleotide primers used to screen the resistant stem cell colonies by PCR. H represents the hybridization probe for the PCR fragment.

As indicated above, a segment of the genomic sequences from the mouse p53 gene (a 3.7-kb fragment spanning exons 2 to 10 of the 11 exon gene) was obtained from plasmid pSVpcG3 (Pinhasi et al. *Molec. Cell. Biol.* 4:2180–2186 (1984)). As shown in FIG. 1, this sequence of DNA was modified in two ways. First, a neo marker gene driven by the MC1 promoter enhancer was designed to obtain high levels of expression in ES cells (Thomas, K. R. et al., *Cell* 51:503–512 (1988)). This sequence was inserted into the unique Bal 1 site in exon 5. This insertion provided a positive selectable marker (neo) for stable gene transfer into ES cells and disrupted the coding sequence of p53, producing an inactive allele following successful homologous recombination. The second alteration entailed the attachment of a herpes simplex virus thymidine kinase gene (HSV TK) to the 3' end of the gene-targeting construct (FIG. 2). This attachment provided the negative selection (using the HSV-TK-specific thymidine analogue FIAU (1-(2 deoxy, 2 fluoro, β-D arabinofuranosyl)-5-iodouracil) against cells that have random integrations of the targeting construct (FIG. 2).

EXAMPLE 3

Transfer of Constructs into ES Cells and Identification of Cells Containing Homologous Recombination Events After generating the above-described p53 targeting construct (FIG. 2), the construct was introduced into cultured ES cells by electroporation. ES cells were cultured as described by E. J. Robertson (In: *Teratocarcinomas and Embryonic Stem Cells: A Practical Approach*, (E. J. Robertson, Ed.), IRL Press, Oxford, 1987, pp 71–112). Cells for electroporation were collected by trypsinization at 60–80% confluency, sedimented and resuspended in buffered saline with DNA at 25 U/ml. $10^7$ cells/ml are treated with a single pulse from a Bio-Rad Gene Pulser (0.240 volts, 500 uF, 0.4 cm cuvette) in order to achieve electroporation. Under these conditions, efficiencies of stable gene transfer of approximately $10^{-3}$ were obtained. After pulsing, the ES cells were plated onto feeder cells (as described above) at 5×106 cells/6-cm plate for G418/gancyclovir selection. Selection was allowed to proceed for 10–12 days (until control plate showed no colonies).

G418/FIAU-resistant companies were isolated, amplified, and genomic DNA purified from about 50–100 individual isolates. These DNAs were restricted with Hind III, Eco RI, and Pvu II. Colonies were separated into two halves; one half of each colony was lysed with detergent and subjected to PCR with oligonucleotide probes derived from the neo gene and p53 gene sequences outside the borders of the targeting construct. If the insertion of the construct had occurred through homologous recombination, then a 1.2 kb fragment would be generated. Two of 100 colonies tested gave the expected 1.2 kb PCR band. The DNA from these positive colonies were then subjected to agarose gel electrophoresis, Southern blotting, and hybridization to three probes. The probes used were a p53 exon 4 probe (130 bp), an exon 11 probe (200 bp), and the neo probe (1 kb). Each of these probes hybridized to Southern fragments diagnostic for a homologous recombination event. Taken together, the Southern hybridization conclusively identified colonies with p53 gene disruptions generated by homologous recombination.

Initial constructs utilized an MC1-neo gene; these constructs did not work well. The successful constructs were a -Pol II-neo-polyA⁻- gene construct.

EXAMPLE 4

Construction of Mouse Chimeras from Specific ES Cell Clones

Chimeras were constructed from suitable clones as described by Bradley, A. (In: *Teratocarcinomas and Embryonic Stem Cells: A Practical Approach*, (E. J. Robertson, Ed.), IRL Press, Oxford, 1987, pp 113–151). Briefly, 3.5-day-old blastocyst-stage embryos were collected from the dissected uterine tracts of C57BL females 3 days after plugging. 12–15 individual cells were microinjected into the cavity of the blastocyst-stage embryos and, after a brief culture period, transferred back into the uterine horns of pseudopregnant $F_1$(CBA×C57BL) foster mothers 2 days after mating with a vasectomized male.

The methods for introducing the ES cell into the blastocyst, and for producing offspring have been described above, and comprise techniques which are well-known to those of ordinary skill (Mansour, S. L. et al., *Nature* 336:348–352 (1988); Capecchi, M. R., *Trends Genet.* 5:70–76 (1989); Capecchi, M. R., *Science* 244:1288–1292 (1989); Capecchi, M. R. et al., In: *Current Communications in Molecular Biology*, Capecchi, M. R. (ed.), Cold Spring Harbor Press, Cold Spring Harbor, N.Y. (1989), pp. 45–52; Frohman, M. A. et al., *Cell* 56:145–147 (1989); all of which references have been incorporated herein by reference).

In order to generate an adequate number of chimeras of high quality (i.e., high contribution of donor cells) the blastocyst injection experiments were repeated over a period of a few weeks. Approximately 53 blastocyst injections were performed.

Following embryo transfer, the young are born 17 days later. The levels of chimerism could not be assessed at this time because the cell line used carries the Black Agouti coat color markers and the embryos are Black non-Agouti. The Agouti marker becomes visible in the coat at day 8. At this stage the chimeras were scored and non-chimeric animals discarded. The presence of the Y chromosome in the donor cell line ensured that the majority of any germ line contribution was through the germ line of male chimeras. In addition, dominant effects of the Y chromosome distort the sex ratio among the chimeric offspring in favor of males by the conversion of some female embryos to phenotypic males. The sex ratio consequently is an effective early measure of the levels of chimerism in the experimental population, and this tends to reflect germ line chimerism.

The mice ranged from total black (i.e. no chimerism) to greater than 90% agouti (i.e. very high chimerism). When the above-described stromal feeder cell procedures were employed, greater than 50% of the injected pups showed high degrees of chimerism (as determined by the ratio of agouti coat color to black coat color in the offspring).

EXAMPLE 5

Test Breeding of Chimeras to Assay for Germ Line Contributions and Identification of Heterozygotes Of the 53 injected blastocysts, approximately 12 male mice were obtained which exhibited high to very high chimerism (i.e. levels of contributions of agouti hair in their coat that exceeded 50%). These mice were subjected to inbreeding and further analysis as described below.

The 12 male chimeric mice were test bred when they reached sexual maturity (about 8 weeks of age). Test breeding proceeded by caging a single germ line chimera with two virgin C57BL females, and permitting the animals to naturally breed. Successive litters were scored after 8 days of age. The presence of the dominant Agouti coat color among the litter demonstrated the successful colonization of the germ line. This approach assumed, that, as in the case of the rb gene, a single normal germ line allele would be able to supply normal p53 function and that gene dosage effects would not be important.

Unexpectedly, this assumption was not confirmed. Of the 12 chimetic mice, only four mice (#96, #101, #102 and #103) were found to produce progeny mice. The great majority of these mouse pups (approximately 95–97%) died at about 24 hours post partum. Nevertheless, after several litters, five viable pups, designated p1–p5 were obtained from parents #101 and #102. These parental mice (#101 and #102) were found to be equivalent for the purposes of the invention. The five mice pups were grown to adolescence, and are fully viable.

The 5 mice pups were tested by Southern blot hybridization of tail DNA to determine whether they contained the mutated p53 allele. Thus, when the pups reached six to eight weeks of age, approximately one inch of tail was snipped off and used to prepare high molecular weight DNA according to the following protocol for the preparation of high molecular weight DNA from mouse embryo and/or yolk sacs:

In the procedure, it is desirable to reserve materials and solutions (such as Eppendorf tubes, proteinase K, distilled water (dH₂O), phenol, phenol/chloroform, chloroform, isopropanol, TE, etc.) for genomic use, and to then use such materials only when preparing samples of genomic DNA.

Steps of the Protocol:

1. The embryos of the required gestation are carefully isolated from maternal tissue. The embryos and/or yolk sacs are then placed into Eppendorf tubes containing 250 μl of Cutting Buffer (50 mM Tris pH 7.5, 50 mM EDTA pH 8.0, 100 mM NaCl, 5 mM DTT, 0.5 mM Spermidine). The embryos can either be processed singly or fixed for staining, using their respective yolk sacs for the isolation of DNA.
2. The embryonic tissue is finely minced with a scissors. It may, alternatively, be broken up by passing it twice through a 26G ⅝" Sub-Q needle attached to a 1 cc syringe. Yolk sac is very soft tissue that is easily broken up during lysis; therefore, no further manipulation is necessary.
3. 250 μl of Lysis Buffer (50 mM Tris pH 7.5, 50 mM EDTA pH 8.0, 100 mM NaCl, 5 mM DTT, 0.5 mM Spermidine, 2% SDS) and 10 μl of freshly prepared 10 mg/ml Proteinase K is added to each tube.
4. The tubes are gently rocked overnight at 55° C.
5. 500 μl of phenol is added to each tube, and the tubes are rotated at 5–10 rpm for 15–20 minutes. The tubes are then centrifuged in a microcentrifuge at maximum speed for 10 minutes. The DNA is then transferred to clean Eppendorf tubes using pipette tips from which the tips have been snipped off. [When pipetting genomic DNA samples, it is preferable to use pipette tips from which the tips have been snipped off. This will prevent shearing the DNA and keep the average size in excess of 80–100 kb.]
6. 500 μl of phenol/chloroform is added to each tube, and step 5 is repeated.

7. 500 μl of chloroform is added to each tube, and step 5 is repeated. When transferring the DNA to clean tubes, the volume transferred is to be recorded.
8. A volume of isopropanol equal to the volume of DNA is added to each tube. The tubes are inverted a few times to precipitate the DNA.
9. The tubes are centrifuged in a microcentrifuge at maximum speed for 10 minutes.
10. The supernatant is carefully aspirated off. The pelleted DNA is rinsed in 1 ml of 70% of ethanol (EtOH). The tubes are centrifuged again in the microcentrifuge at maximum speed for 10 minutes.
11. The EtOH is poured off and allow the pellets are allowed to air dry until there is no visible sign of remaining EtOH. The DNA is resuspended in 15 μl of TE buffer (10 mM Tris pH 8.0, 1 mM EDTA pH 8.0).
12. Enough DNA can be prepared for at least one lane of a 20 cm×15 cm agarose gel with 30 sample wells; usually, a couple of hundred micrograms of DNA is obtained. The DNA is digested by adding 2 μl of the appropriate 10× buffer, 2 μl of dH$_2$O, and 1 μl of the appropriate restriction enzyme (i.e., such that the reaction is in 20 μl total volume).
13. Since genomic DNA is difficult to load in this size of well (in which it has to displace the electrophoresis buffer), the gel is loaded at the bench before it is submerged in the running buffer.

Once the DNAs were obtained, their concentrations were determined by A$_{260}$ determination on a UV spectrophotometer. 5–10 μg of the DNAs were then cleaved with either BamHI or EcoR1 restriction endonucleases for several hours at 37° C. The cut DNAs were loaded on a 0.8% agarose gel and electrophoresed at 100 V for approximately 3 hours on a horizontal submarine gel apparatus. The DNAs were then blotted to Zetaprobe (BioRad) nylon membranes and hybridized in 20% dextran sulfate-3×SSPE, both steps according to the protocol of Reed and Mann (Reed, K. C. et al., *Nucleic Acids Res.* 13:7207–7221 (1985)). The probe for hybridization was $^{32}$P-labelled according to the protocol of Feinberg and Vogelstein (Feinberg, A. et al., *Anal. Biochem.* 132:6–13 (1983)). Hybridization was permitted to continue overnight at 68° C. and the filters were washed according to the protocol of Reed and Mann (Reed, K. C. et al., *Nucleic Acids Res.* 13:7207–7221 (1985))). The probe for FIG. 4 was a pol II-neo probe. The Pol II part of the probe hybridizes to a 4.0 kb fragment of the Pol II gene which is present in all mice. The Neo part of the probe hybridizes to a larger 6.7 kb fragment present only in the p53 targeted germ line heterozygote mice.

Figure 4:
FIG. 4 shows a Southern blot analysis of tail DNA of the progeny of the $F_1$[129×C57BL/6] chimeric mice. The analysis reveals that mouse pups p1 and p3 contain DNA which hybridizes to the neogene, and thus contains the mutated p53 construct. "+" indicates positive control (i.e. embryonic stem cell with disrupted p53 gene); "–" indicates negative control (i.e. normal mouse DNA).

Two of the five mice tested, pups p1 and p3, were found to contain the mutated p53 allele in its germ line (FIG. 4). FIG. 4 shows a Southern blot analysis of tail DNA of the progeny of the F$_1$[129×C57BL/6] chimeric mice. The DNA was restricted with BamHI and hybridized to the above-described $^{32}$P-labelled Pol II-Neo probe. The band between the offspring and the controls is a marker which happened to hybridize to the probe. The analysis thus revealed that mouse pups p1 and p3 contain DNA which hybridizes to the neo gene, and thus contain the mutated p53 construct.

Following the demonstration of germ line chimericism, the initial F$_1$(C57BL×129) males were crossed with strain 129 females to generate a larger population of heterozygote mice. Germ line transmission of the mutated p53 allele to offspring may be confirmed by restriction mapping analysis.

Thus, in summary, 4 of the 12 mice exhibiting very high chimerism (#96, #101, #102 and #103) were found to be good breeders, when permitted to breed naturally. Of these four mice, mice #101 and #102 were found to produce viable offspring having the agouti phenotype. Thus, these chimeric mice have been demonstrated to be germ line chimeric animals (i.e. they contain germ cells which possess the desired p53 construct, and are capable to transmitting this construct to progeny animals). Indeed, progeny animals of mice #101 and #102 were obtained, through routine breeding. Two of these progeny animals (p1 and p3) contained the mutated p53 allele in its germ line, and were thus capable of transferring it indefinitely to future generations by further routine breeding.

EXAMPLE 6

Figure 5:
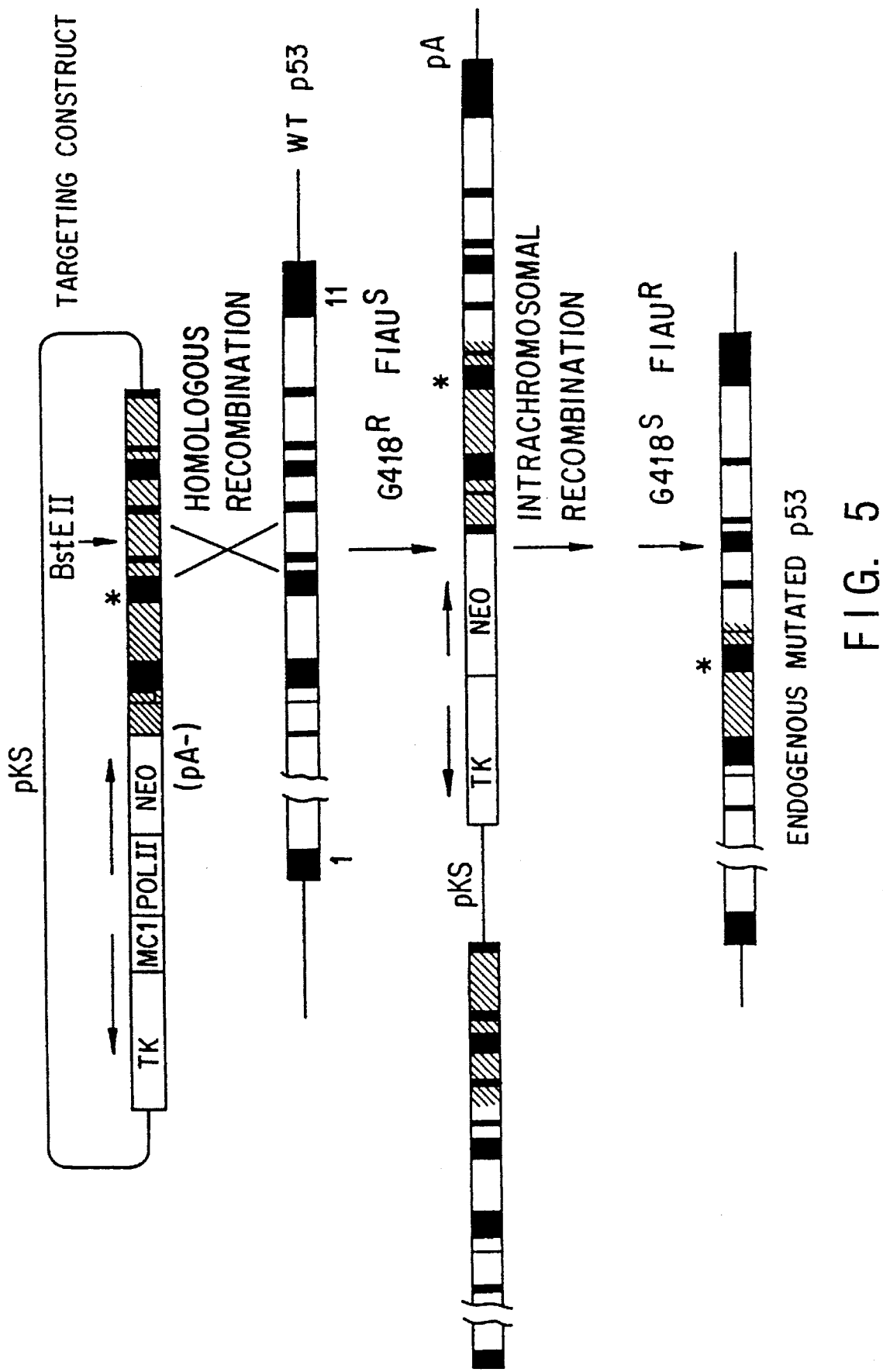
FIG. 5 shows the procedures which are used to produce any desired mutation into a p53 allele of a cell.

Production of Transgenic Animals Having LI-Fraumeni and Other p53 Mutant Alleles The above-described non-human transgenic animal contains a mutation in the p53 gene. The same methods can be used to produce animals having other mutations in this gene (FIG. 5). Thus, a targeting construct is prepared which contains a desired mutation (deletion, insertion or point mutation). The construct is introduced into embryonic stem cells, and permitted to undergo homologous recombination with a p53 allele of that cell. This process leads to the integration of the construct into the p53 locus of the stem cell, and results in a duplication of the p53 gene at that locus. The duplication is resolved, via intrachromosomal recombination to yield an embryonic stem cell having the desired mutated p53 allele (FIG. 5).

EXAMPLE 7

Assay of Tumor Frequency in the Heterozygous Animals

A sizable group (n=50–100) of F$_1$ mice with a single disrupted p53 allele are observed over a period of 12–24 months for signs of spontaneous tumors, abnormal symptoms, or early deaths. Careful records of deaths and tumor incidence are kept and compared to a control population of F$_1$ mice that are homozygous for the normal p53 allele. Mice are sacrificed at 3, 6, 12, and 18 months of age and autopsied for any unusual histopathology. Mice exhibiting distress, disease symptoms, or evidence of tumors are sacrificed and examined to establish the exact nature of disease.

Groups of mice are treated with a known carcinogen, such as DMBA, following standard procedures (Butel, J. S. et al., *J. Virol.* 38:571–580 (1981); Knepper, J. E. et al., *Intl. J. Canc.* 40:414–422 (1987), both of which references are herein incorporated by reference) and observed for tumor development.

The transgenic mice are infected with Friend murine leukemia virus (F-MuLv) and assayed for time of onset and severity of erythroleukemia. F-MuLv integration into one or both alleles of the p53 gene is associated with erythroleukemia in virus-infected mice (Mowat et al., *Nature* 314:633–636 (1985); Chow et al., *J. Virol.* 61:2777–2781 (1987); Hicks, G. G. et al., *J. Virol.* 62:4752–4755 (1988)).

When differences in tumor incidence between normal mice and heterozygotes are observed, the data is analyzed by standard statistical procedures to determine the significance of the results. Significant increases in tumor incidence in the p53 heterozygote mice is preferably established using larger scale confirmatory studies and carcinogen sensitivity studies documenting the utility of the mice as research and carcinogen screening tools.

The transgenic mice are inter-bred, by conventional, non-recombinant methods, in order to determine whether p53 is a recessive lethal gene and, if so, to determine what stage of embryogenesis is affected. If development proceeds significantly, the organs and issues most affected are identified. Tumors derived from p53 heterozygotes are screened to determine the range of mutations in the remaining "normal" p53 allele. Embryo fibroblast cultures are derived from the altered animals to determine which parameters of transformation are affected under normal culture conditions and following transfection with oncogenes or treatment with carcinogens.

The p53 heterozygotes are interbred to obtain transgenic animals in which both of the animal's p53 alleles contain the mutated construct.

The p53 heterozygotes are bred to other transgenic mice containing activated dominant oncogenes (e.g., the transgenic mouse of Leder, P. et al. (U.S. Pat. No. 4,736,866)) to determine whether offspring containing both mutant genes have an accelerated rate of tumor formation.

EXAMPLE 8

Characterization of the p53-Deficient Mice

The above-described p53 heterozygous mice were obtained and interbred to produce progeny. Among the progeny identified were p53 homozygous animals. Thus, unexpectedly, the present invention permitted the isolation and propagation of both p53 heterozygous mice and p53 homozygous mice.

A. p53-Homozygotes Have No Intact p53 RNA or Protein

Figure 6A:
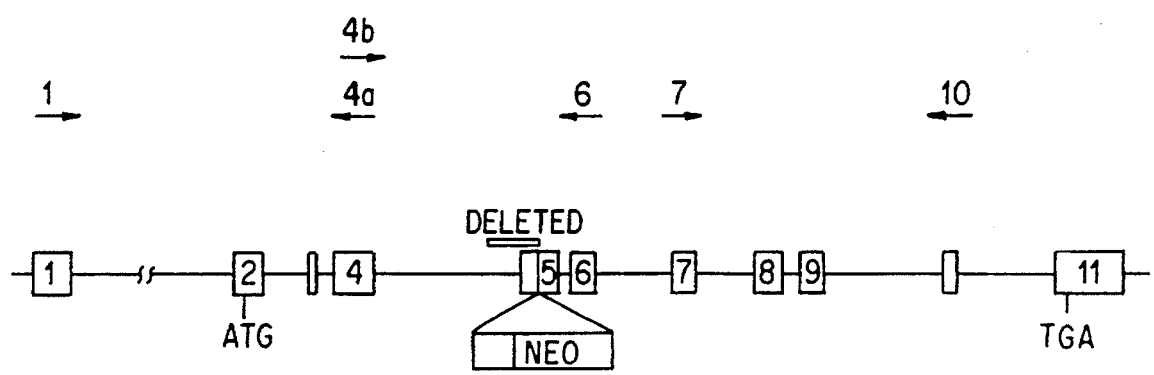
FIG. 6A shows the location and orientation of the primers used in the PCR amplification of the p53 mRNA.
Figure 6B:
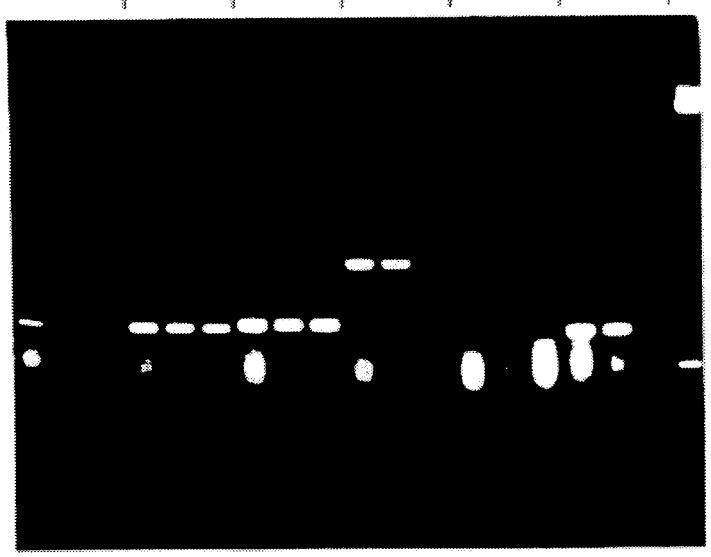
FIG. 6B shows the results of the PCR amplification. The gel shows 19 lanes, of which the last (M) contains molecular size markers. The initial 18 lanes depict the amplification obtained in normal mice (++), p53 heterozygote mice (+–), and p53 homozygote mice (––), respectively, with each of six different pairs of PCR primers (1 and 4a; 7 and 10; B-actin control; 4b and 10; 1 and 10; and 4b and 6). The appearance of a band indicates that the primer pairs amplified a segment of an mRNA species present in the preparation.

To conclusively show that the gene targeting of the p53 allele in the mouse germ line generated a null mutation, p53 RNA and protein were analyzed from homozygote tissues and cells. The rationale was that no intact p53 RNA or protein should be present if the disrupted p53 gene was completely inactivated. To assess p53 RNA levels in the homozygotes, RNA-PCR procedures were used because tissue p53 RNA levels are often so low that Northern analyses are inadequate for detection. Five sets of primers (FIG. 6A) were used to amplify cDNA synthesized from total RNA purified from spleen, kidney, and testes of wild type, heterozygote, and homozygote mice. The results of these RNA-PCR assays using total spleen RNA (FIG. 6B) clearly indicated that an intact p53 mRNA was synthesized only in the wild type and heterozygote mice. Note that for the primers which amplify a fragment spanning the exon 5 neo insertion site there is no apparent PCR fragment in the homozygotes, indicating the failure of the homozygotes to produce an intact message. However, exon 7 and 10 primers generate a strong fragment from the homozygotes cDNA. The data supports the conclusion that the RNA generated 3' of the neo insertion site is part of a hybrid neo p53 message initiated by the pol II promoter. Exon 1 and 4 primers amplified a very faint PCR band from the homozygote cDNAs relative to the wild type cDNAs. The low amounts of this band indicates that transcription from the endogenous p53 promoter in the homozygotes appears to result in an unstable truncated transcript as a result of the neo cassette insertion.

To demonstrate that a normal p53 protein is not expressed in the homozygotes, an immunoprecipitation assay was performed on proteins derived from tertiary embryo fibroblasts obtained from normal, heterozygote, and homozygote embryos. Using a polyclonal p53 antiserum, the wild type and heterozygote cells were found to contain a precipitable p53, while the homozygote cells did not.

In order to further investigate whether any intact or truncated p53 molecule was expressed in the homozygotes, an immunoblot analysis was performed using a control antibody (E1a-specific antibody M73 (Harlow, E. et al., *J. Virol.* 55:533–546 (1985)) and three different p53-specific monoclonal antibodies selected from a set of six such antibodies: PAb 242 (Yewdell, J. W. et al., *J. Virol.* 59:444–452 (1986)); PAb 246 (Yewdell, J. W. et al., *J. Virol.* 59:444–452 (1986)); PAb 248 (Yewdell, J. W. et al., *J. Virol.* 59:444–452 (1986)); PAb 421 (Harlow, E. et al., *J. Virol.* 39:861–869 (1981)); RA3.2C2 (Coffman, R. L. et al., *J. Exper. Med.* 153:269–279 (1981)); and 200.47 (Dippold et al., *Proc. Natl. Acad. Sci. (U.S.A.)* 78:1695–1699 (1981)). The epitopes identified by these antibodies have been mapped (Gannon, J. V. et al., *EMBO J.* 9:1595–1602 (1990); Wade-Evans, A. et al., *EMBO J.* 4:699–706 (1985); Mole, S. E. et al., *Nucl. Acids Res.* 17:3319 (1989); Yewdell, J. W. et al., *J. Virol.,* 59:444–452 (1986)). Cell lysates were initially immunoprecipitated with a collection of either (1) PAb 242, PAb 246, and PAb 248, mapping to the p53 epitope located at amino acids 14–25, 88–109, and 14–69, respectively, or (2) PAb 421, RA3.2C2, and 200.47, mapping to the p53 epitope located at amino acids 370–378, 41–69, and 41–111, respectively. The immunoprecipitates were then subjected to SDS polyacrylamide gel electrophoresis, followed by transfer of the proteins to nylon. These blots were then probed with all six of the above-mentioned anti-p53 monoclonal antibodies. The results clearly indicated that homozygotes did not contain any intact or truncated p53 detectable by this assay.

In conclusion, the RNA and protein data indicate that neither intact or truncated p53 is produced in the homozygotes and that the targeted p53 mutation indeed represents a null mutation.

B. p53-Homozygote Mice are Susceptible to Tumors

Although the p53-negative homozygous mice appeared developmentally normal, they were clearly susceptible to spontaneous tumor formation (naturally occurring tumors are rare in mice less than 6 months of age (Madison, R. M et al., *J. Nat'l. Canc. Inst.* 40:683–685 (1968); Maita, K. et al., *Toxicol. Pathol.* 16:340–349 (1988); Squire, R. A. et al., In: *Pathology of Laboratory Animals, Volume II,* (Eds., Benirshke, K. et al.), 1054–1055 (Springer-Verlag, NY, 1978)).

The chimeric mice and the germ line p53 heterozygotes and homozygotes were monitored daily for tumors or other abnormalities. The incidence of tumors was noted when the chimeric mice were 14 months old, the oldest heterozygotes were over nine months old and the oldest homozygotes were about six months old (Table 1, age is in weeks (wks) or months (mons)). At that time, no tumors were observed in the normal control mice, a variety of tumors were detected in the homozygote mice (Table 1; cases #1–20), two tumors were detected in the heterozygote mice (Table 1, cases #21 and #22), and three tumors were detected in the chimeric mice (Table 1, cases #23 and #24; in case #23, the phenotypically male mouse had a choriocarcinoma surrounded by recognizable ovarian tissue).

TABLE 1

TUMORS OBSERVED IN p53-DEFICIENT MICE

| # | Sex | Age | Histologic type | Anatomic site |
|---|---|---|---|---|
| 1 | M | 18 wks | undifferentiated sarcoma | subcutis |
| 2 | M | 8 wks | gonadoblastoma | testes |
|   |   |       | malignant lymphoma | thymus |
| 3 | M | 18 wks | hemangiosarcoma (2) | subcutis/liver |
| 4 | F | 9 wks | malignant lymphoma | generalized |
| 5 | F | 15 wks | malignant lymphoma | generalized |
| 6 | M | 24 wks | undifferentiated sarcoma | vertebra |
|   |   |       | hemangiosarcoma | subcutis |
| 7 | M | 24 wks | hemangiosarcoma | subcutis/muscle |
|   |   |       | malignant lymphoma | generalized |
| 8 | M | 15 wks | hemangiosarcoma | subcutis |
| 9 | M | 24 wks | hemangiosarcoma | subcutis |
|   |   |       | malignant lymphoma | generalized |
| 10 | M | 16 wks | osteosarcoma | pelvis |
| 11 | F | 15 wks | malignant lymphoma | generalized |
|    |   |       | hemangioma | heart |
| 12 | F | 18 wks | malignant lymphoma | thymus |
| 13 | M | 14 wks | malignant lymphoma | generalized |
| 14 | F | 14 wks | malignant lymphoma | generalized |
| 15 | F | 15 wks | mammary adenocarcinoma | mammary gland |
| 16 | M | 16 wks | malignant lymphoma | generalized |
|    |   |       | hemangiosarcoma | subcutis |
|    |   |       | hemangioma | muscle |
| 17 | M | 17 wks | malignant lymphoma | generalized |
| 18 | M | 17 wks | malignant lymphoma | generalized |
|    |   |       | hemangiosarcoma (2) | heart/perirenal fat |
| 19 | M | 21 wks | malignant lymphoma | thymus |
| 20 | M | 22 wks | malignant lymphoma | generalized |
| 21 | M | 24 wks | embryonal carcinoma | testis |
| 22 | M | 37 wks | malignant lymphoma | generalized |
| 23 | M | 14 mons | osteosarcoma | sacrum |
|    |   |       | choriocarcinoma | ovary* |
| 24 | M | 14 mons | Leydig cell tumor | testis |

More than 70 wild type mice, 100 heterozygotes, and 60 homozygotes have been analyzed. The data collected on the mouse tumors indicate that homozygote mice are susceptible to tumors at an early age. By six months, greater than 50% of homozygotes develop tumors. Thus, the tumor incidence in such mice is considerably higher than the 20% incidence observed by 18 months of age in mice carrying a mutant p53 transgene (Lavigueur, A. et al., *Molec. Cell. Biol.* 9:3982–3991 (1989)). Four of the homozygote mice were found to have had multiple primary tumors of different cell type origin. The tumors in the older chimeric and heterozygote mice suggest that mice with a single mutant p53 allele are also susceptible to tumors, but at a decreased rate compared to homozygotes. No wild type control mice have developed tumors currently under observation. These results thus support the conclusion that loss of one or both p53 alleles predispose the mice to cancer. The variety of tumors identified in the homozygote mice demonstrate that p53 is involved in tumorigenesis in many tissues and cell types.

Despite having a developmentally normal appearance, a significant number of the homozygous animals succumbed to premature death in the absence of obvious tumors (tissue autolysis prevented a complete pathological analysis in some cases). Several of the deaths appeared associated with unresolved infections, suggesting the presence of a subtle defect of the immune system in the homozygotes. Such immune defects, thus appear able to contribute to the accelerated rate of tumor development in these animals.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A transgenic mouse whose somatic and germ line cells contain a genome comprised of two alleles of the tumor suppressing p53 gene, one of the alleles being disrupted by a selectable marker sequence, wherein the mouse is more susceptible to developing tumors than the wild type mouse.

2. A transgenic mouse whose somatic and germ line cells contain a genome comprised of two alleles of the tumor suppressing p53 gene, both of the alleles being disrupted by a selectable marker sequence, wherein the mouse is more susceptible to developing tumors than either the heterozygous mouse comprised of a disruption by a selectable marker sequence in one p53 allele or the wild type mouse.

3. A transgenic mouse whose somatic and germ line cells contain a genome comprised of two alleles of the tumor suppressing p53 gene, one of the alleles being disrupted by a selectable marker sequence in exon 5, wherein the mouse is more susceptible to developing tumors than the wild type mouse.

4. A transgenic mouse whose somatic and germ line cells contain a genome comprised of two alleles of the tumor suppressing p53 gene, both of the alleles being disrupted by a selectable marker sequence in exon 5, wherein the mouse is more susceptible to developing tumors than either the heterozygous mouse comprised of a disruption by a selectable marker sequence in one p53 allele or the wild type mouse.

\* \* \* \* \*